US007335501B1

(12) United States Patent
Pierrard et al.

(10) Patent No.: US 7,335,501 B1
(45) Date of Patent: Feb. 26, 2008

(54) PHYTASES AND METHODS FOR PRODUCING THESE PHYTASES

(75) Inventors: Jerome Pierrard, Saint Didier Au Mont D'or (FR); Ralph Bohlmann, Lyons (FR); Olivier Nore, Azay sur Cher (FR); Didier Saunier, Montlucon (FR); Olivier Testeniere, Dijon (FR); Fanny Moussu, Saint Laurent En Gatines (FR)

(73) Assignee: Adisseo France S.A.S., Antony (FR)

( * ) Notice: Subject to any disclaimer, the term of this patent is extended or adjusted under 35 U.S.C. 154(b) by 257 days.

(21) Appl. No.: 10/864,369

(22) Filed: Jun. 10, 2004

Related U.S. Application Data

(63) Continuation-in-part of application No. PCT/EP02/14863, filed on Dec. 10, 2002.

(30) Foreign Application Priority Data

Dec. 10, 2001 (FR) .................................. 01 15954

(51) Int. Cl.
| | |
|---|---|
| *C12Q 1/68* | (2006.01) |
| *C12N 9/16* | (2006.01) |
| *C12N 15/70* | (2006.01) |
| *C12N 1/21* | (2006.01) |
| *C12N 15/74* | (2006.01) |
| *C12P 21/06* | (2006.01) |
| *C07H 21/04* | (2006.01) |

(52) U.S. Cl. ............... 435/196; 435/69.1; 435/252.32; 435/252.35; 435/254.3; 435/252.3; 435/254.21; 435/254.2; 435/320.1; 435/252.33; 435/254.5; 435/254.11; 435/483; 435/484; 435/254.6; 435/254.23; 536/23.2

(58) Field of Classification Search ................ 435/196, 435/6, 69.1, 320.1, 252.33, 254.5, 254.11, 435/483, 484; 536/23.2
See application file for complete search history.

(56) References Cited

FOREIGN PATENT DOCUMENTS

| | | |
|---|---|---|
| EP | 0 955 362 A1 | 11/1999 |
| JP | 7-67635 | 3/1995 |
| WO | WO 97/35016 | 9/1997 |
| WO | WO 01/12792 A1 | 2/2001 |

OTHER PUBLICATIONS

Pen, J. et al., "Phytase-containing Transgenic Seeds as a Novel Feed Additive for Improved Phosphorus Utilization," Bio/Technology, vol. 11, No. 7, Jul. 1993, pp. 811-814.

*Primary Examiner*—Rebecca E. Prouty
*Assistant Examiner*—Iqbal Chowdhury
(74) *Attorney, Agent, or Firm*—Oliff & Berridge PLC

(57) ABSTRACT

The present invention relates to novel phytases, in particular, of fungal origin, and also to their respective methods of production. The present invention relates more particularly to novel phytases derived from fungi of the *Penicillium* genus, in particular of the *Penicillium* sp. CBS 109899 strain, and also to the polynucleotides encoding these phytases. The invention also relates to vectors containing the polynucleotides, and to transformed host organisms expressing the phytases.

40 Claims, 2 Drawing Sheets

PHYTASES AND METHODS FOR PRODUCING THESE PHYTASES

This is a Continuation-in-Part of International Application No. PCT/EP02/14863 filed Dec. 10, 2002. The entire disclosure of the prior application is incorporated by reference herein in its entirety.

The present invention relates to novel phytases, in particular of fungal origin, and also to their respective methods of production. The present invention relates more particularly to novel phytases derived from fungi of the *Penicillium* genus, in particular of the *Penicillium* CBS 109899 strain, and also to the polynucleotides encoding these phytases. The invention also relates to vectors containing these polynucleotides, and to transformed host organisms expressing said phytases in their tissues.

In particular, the phytases of the present invention are particularly suitable for use in feed compositions intended for animal nutrition. This suitability is associated with their properties, in particular their activity under conditions of temperature and pH corresponding to the conditions for preparing said compositions and also those encountered in the digestive system of animals.

Phosphorus is an element essential to the life of all organisms. In particular, it is of the utmost importance for farm animal breeders to be sure that their animals ingest a sufficient amount thereof to optimize their growth and development. Most farm animals are fed with plant-based feed compositions. These plants contain large amounts of phosphate which they store in their tissues in the form of a storage compound, phytic acid. On average, phytic acid contains 50 to 70% of the phosphorus present in plants. Phytic acid is naturally mobilized and the phosphate which it contains is released in most farm animals, in particular ruminants. However, phytic acid is not metabolized by monogastric animals such as pigs and poultry. In these animals, the phytic acid contained in their food intake is therefore discharged with the excrements, and the breeder has to supplement said intake with inorganic phosphate so that his animals ingest a sufficient amount of phosphorus. This strategy engenders additional expenditure for the breeder and generates pollution derived from the discharge into the environment of the non-assimilated phytic acid. This pollution is increased all the more in areas of intensive breeding.

Phytic acid is also known to be a chelator of important nutritive elements contained in the food intake, such as, for example, magnesium, calcium, zinc or iron. This property leads to a decrease in the nutritive quality of the food intake, giving phytic acid the property of an antinutritional agent.

In order to respond to the various drawbacks associated with the lack of assimilation of phytic acid by monogastric animals, the introduction of an enzyme, phytase, into the food intake of these livestock animals has been envisioned. Phytase hydrolyzes phytic acid, releasing inositol and inorganic phosphate. Phytases, and the genes encoding these phytases, have been isolated from many organisms. Phytases have mainly been isolated from fungi (Howson and Davis, 1983, Enzyme Microb. Technol. 5, 377-382; Wyss et al., 1999, Appl. Environ. Microbiol., 65(2), 359-366). Among the fungi which produce a phytase, mention may be made of fungi of the *Aspergillus* genus, in particular *A. ficcum* (Ullah and Gibson, 1987, Preparative Biochemistry 17(1), 63-91; Ullah and Dischinger, 1993, Biochem. Biophys. Res. Commun., 192(2), 747-753), *A. terreus* (Mitchell et al., 1997, Microbiology, 143 (Pt 1), 245-252), *A. niger* (Dvorakova et al., 1997, Folia Microbiol (Praha), 42(4), 349-352), *A. fumigatus* (Pasamontes et al., 1997, Appl. Environ. Microbiol., 63(5), 1696-1700), of the *Penicillium* genus, in particular *P. caseicolum*, of the *Myceliophthora* genus, in particular *M. thermophila* (Mitchell et al., 1997, Microbiology, 143 (Pt 1), 245-252), of the *Talaromyces* genus, in particular *T. thermophilus*, of the *Neurospora* genus, in particular *N. crassa* and *N. sitophila*, of the *Thermomyces* genus, in particular *T. lanuginosus* (Berka et al., 1998, Appl. Environ. Microbiol. 64(11), 4423-4427), or of the *Monascus* genus, in particular *M. anka*. Phytases have also been found in bacteria. By way of example, mention may be made of bacteria of the *Bacillus* genus, in particular *B. subtilis* (Powar and Jagannathan, 1982, J. Bacteriol. 151(3), 102-1108; Shimizu, 1992, Biosci. Biotech. Biochem. 56(8), 1266-1269; Keruvo et al., 1998, Appl. Environ. Microbiol. 64(6), 2079-2085), *Pseudomonas* genus (Cosgrove, 1970, Austral. J. Biol. Sci. 23, 1207-1220), *Escherichia* genus, in particular *E. coli* (Golovan et al., 2000, Can. J. Microbiol. 46, 59-71), *Enterobacter* genus (Yoon et al., 1996, Enzyme and microbiol. Technol.; 18, 449-454), or *Streptomyces* genus. Yeast phytases have also been isolated (Dvorakova, 1998, Folia Microbiol. 43(4), 323-338), such as those of the yeasts Schwaniiomyces occidentalis and *Saccharomyces cerevisiae*. Finally, phytases have been found in plants, in particular in soybean (Ullah and Gibson, 1988, Arch. Biochem. Biophys., 260(2), 514-20), in maize (Maugenest et al., 1997, Biochem J., 322 (Pt 2), 511-7); Maugenest et al., 1999, Plant Mol. Biol., 39(3), 503-14), or in *Arabidopsis* (Mullaney and Ullah, 1998, Biochem. Biophys. Res. Commun., 251(1), 252-5).

Properties which make it possible to characterize phytases include the Michaelis constant (Km) with respect to phytic acid, the optimum pH and the optimum temperature for activity, and also the stability of this activity at given pHs and temperatures. Data relating to the structure of phytases can also be used, such as the molecular weight (MW), the isoelectric point (pI) or the peptide sequence. For it to be possible to use them in animal nutrition, phytases must have properties compatible with the processing undergone by the feedstuffs intended for this nutrition. In particular, the activity of the phytases used must be maintained and, if possible, must be optimal under the conditions of temperature and pH of the processes for preparing these feedstuffs, and also those present in the digestive tract of the animals ingesting these feedstuffs. These constraints lead mainly to a search for phytases with activity which withstands high temperature conditions, such as those used in the processes for preparing the feed compositions, and which withstands acid pH conditions, such as those present in the digestive tract of livestock animals.

In order to satisfy these criteria, phytases have been sought in organisms, in particular microorganisms, which develop in environments in which the conditions of temperature and pH correspond to these criteria. This strategy has made it possible to isolate the phytases which withstand high temperatures, such as, for example, those described in patent applications WO 97/35016 or EP 0 684 313, but also of phytases which have a low Km, such as, for example, those described in patent application EP 0 960 934. Another strategy has consisted in artificially modifying the sequence of known phytases by site-directed mutagenesis in order to give it advantageous properties. This strategy has in particular been described in patent applications WO 99/48380, EP 0 897 985 and EP 0 897 010.

DESCRIPTION

Figure 1:
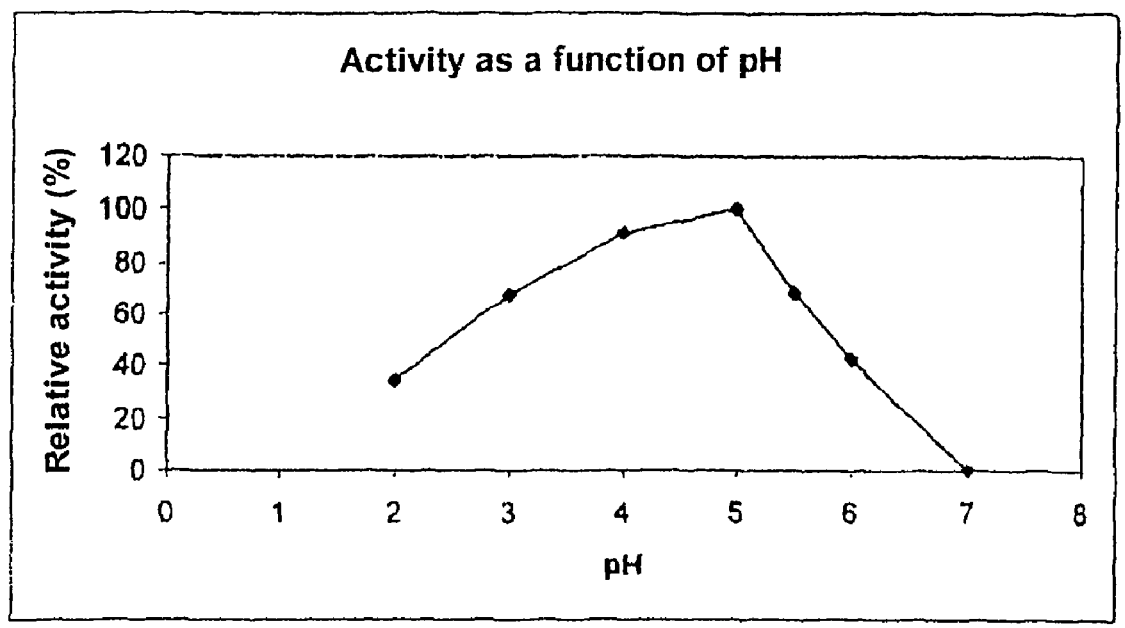
FIG. 1: Activity of the phytase of *Penicillium* sp CBS 109899 as a function of pH. The value 100% of relative activity corresponds to the optimum activity of the phytase for a given pH.

The present invention relates to isolated polynucleotides encoding a phytase described by the sequence identifier SEQ ID NO: 3. This phytase and the polynucleotides which encode it also originate from a fungal strain of the *Penicillium* genus, in particular the *Penicillium* sp CBS 109899 strain.

According to the present invention, the term "polynucleotide" is intended to mean a nucleic acid molecule composed of a natural or artificial sequence of bases which may be of the DNA or RNA type, preferably of the DNA type, in particular double-stranded. When said polynucleotide is natural, it is clearly understood that the invention does not cover this polynucleotide in its natural environment, but the same polynucleotide isolated and purified from the genome of the living organism in which it is naturally found. This polynucleotide may be obtained directly, by extraction and purification, or indirectly by copying. However, the present invention comprises said polynucleotide when it is integrated artificially into the genome of a living organism other than that in which it naturally exists, or when it is artificially reintroduced into the living organism from which it originates, as one or more copies in the genome of this organism. When this polynucleotide is a probe, it is generally single-stranded.

The invention therefore comprises the polynucleotides encoding the peptide sequence of the phytase described by the sequence identifier SEQ ID NO: 3. It is well known to those skilled in the art that this definition includes all polynucleotides which, although comprising nucleotide sequences which are different as a result of the degeneracy of the genetic code, encode the same amino acid sequence, and therefore the same phytase, that is represented by the sequence identifier SEQ ID NO: 3.

The present invention also comprises polynucleotides homologous to the polynucleotides described above, said homologous polynucleotides encoding phytases homologous to the phytase represented by the sequence identifier SEQ ID NO: 3. According to the invention, the term "homologous" is intended to mean polynucleotides encoding phytases, the sequences of which polynucleotides have modifications relative to the polynucleotides encoding the phytase represented by the sequence identifier SEQ ID NO: 3. The homologous polynucleotides are characterized by a degree of identity with the polynucleotides encoding the phytase represented by the sequence identifier SEQ ID NO: 3. The degree of identity between two corresponding polynucleotides is obtained by comparing their sequences, and is generally expressed by a percentage of nucleotides which are identical between these sequences. This degree of identity is measured over a given sequence length, the shorter of the sequences compared determining the length of sequence over which the degree of identity of the homologous sequences is measured. The invention therefore covers polynucleotides having one or more sequence modifications relative to the polynucleotides encoding the phytase represented by the sequence identifier SEQ ID NO: 3, and encoding phytases the properties of which are equivalent to those of the phytase described by the sequence identifier SEQ ID NO: 3.

According to the invention, the expression "equivalent phytases" or "phytases with equivalent properties" is essentially intended to mean proteins having phytase activity, independently of their intrinsic properties such as the Km, the optimum pH for activity or the optimum temperature for activity. The level of phytase activity may be measured by any method for characterizing phytase activity. The term "phytase" is intended to mean an enzyme the catalytic activity of which consists in hydrolyzing phytic acid so as to release inositol and inorganic phosphate. However, since most phytases do not perform a complete hydrolysis of phytic acid (comprising 6 phosphates), the catalytic activity of a phytase according to the invention may lead to the release of inorganic phosphate and of myoinositol phosphate esters, said esters possibly being, depending on the hydrolytic capacity of the phytase, myoinositol mono-, di-, tri-, tetra- or pentaphosphate esters. By way of example, the phytase activity may be measured according to the method of Shimizu (1992, Biosci. Biotech. Biochem. 56(8), 1266-1269), in particular as described in Example 2. However, any method for characterizing a phytase activity, either by measuring the decrease in the amount of substrate or by measuring the accumulation of the products derived from the enzymatic reaction, may be used to measure the phytase activity. In particular, similar methods, using, for example, another substrate or other reagents, also make it possible to measure said phytase activity.

The sequence modifications present in the homologous polynucleotides may be additions, deletions or substitutions of nucleotides which may be natural or obtained by the usual mutagenesis techniques. It is known that such homologous polynucleotides, encoding proteins with equivalent functions, exist naturally in the genomes of different living species, and even in the genomes of different races, varieties or strains. Consequently, it is therefore easy for those skilled in the art, using the teaching of the polynucleotides encoding the peptide sequence represented by the sequence identifier SEQ ID NO: 3 according to the invention, to isolate such homologous polynucleotides using well-known techniques of molecular hybridization (Sambrook et al., 1989, Molecular Cloning: A Laboratory Manual, $2^{nd}$ edition, Nolan C. ed., New York: Cold Spring Harbor Laboratory Press).

Molecular hybridization is a pairing reaction which takes place between complementary strands of polynucleotides having a certain degree of identity between their nucleotide sequences. Hybridization therefore makes it possible, using the polynucleotides encoding the phytase represented by the sequence identifier SEQ ID NO: 3, to identify polynucleotides homologous to these polynucleotides, in the genome of living organisms other than the organism from which they are derived, for example other fungi, in particular other strains of *Penicillium*, for example *P. funicolosum* IMI 134756, and encoding phytases with properties equivalent to the phytase represented by the sequence identifier SEQ ID NO: 3. The greater the sequence identity between polynucleotides, the greater the possibility and ease of hybridization between said polynucleotides, and the greater the probability that the polynucleotides encode proteins with equivalent properties. The methods for hybridizing polynucleotides are widely described in the literature (Sambrook et al., 1989, Molecular Cloning: A Laboratory Manual, $2^{nd}$ edition, Nolan C. ed., New York: Cold Spring Harbor Laboratory Press) and are well known to those skilled in the art. They are, for example, based on screening a genomic or cDNA library created from a living organism or from a tissue of this organism. The screening is carried out using a probe consisting of a known polynucleotide, or a fragment thereof, in order to identify, in these libraries, the polynucleotides homologous to said probe which will hybridize thereto. According to the invention, the probe consists of a polynucleotide encoding the phytase represented by the sequence identifier SEQ ID NO: 3, or a fragment thereof. In order to identify the polynucleotides to which the probe hybridizes, it is labeled, for example with radioactive elements, such as $^{32}P$ Commercially available nonradioactive labels which are well known to those skilled in the art may also be used.

The present invention therefore also comprises polynucleotides capable of hybridizing selectively to one of the polynucleotides encoding the phytase represented by the sequence identifier SEQ ID NO: 3, or a fragment thereof. It is understood that these polynucleotides are only part of the present invention if they encode a phytase equivalent to that represented by the sequence identifier SEQ ID NO: 3. According to the invention, the expression "polynucleotides capable of hybridizing selectively" is therefore intended to mean the polynucleotides which, by one of the usual methods of molecular hybridization, (Sambrook et al., 1989, Molecular Cloning: A Laboratory Manual, $2^{nd}$ edition, Nolan C. ed., New York: Cold Spring Harbor Laboratory Press), hybridize with a labeled probe consisting of one of the polynucleotides encoding the phytase represented by the sequence identifier SEQ ID NO: 3, or a fragment thereof, at a level greater than the nonspecific hybridization of said probe with other relatively nonhomologous polynucleotides, in particular other cDNAs if the polynucleotides probed are derived from a cDNA library. The level of hybridization is measured by virtue of the signal produced by the label of the probe. The level of the signal generated by the interaction between the polynucleotides capable of hybridizing selectively and the probe is generally 10 times, preferably 100 times, more intense than that generated by the interaction of the probe with the other polynucleotides generating a "background noise". The selective hybridization is generally obtained using normal, preferably stringent or very stringent, hybridization and washing conditions (for example hybridization with a buffer containing at least 5×SSC and 1% SDS at approximately 50° C.-60° C., and successive washes with 0.1% SDS and a gradual decrease in the concentration of SSC from 2×SSC to 0.4×SSC and also an increase in the temperature from 20° C. to 50° C.). Those skilled in the art will be able to adjust the hybridization conditions, i.e. essentially the temperature and the salt concentration of the buffers used for the hybridization step and the washing step. These conditions should in particular be adjusted as a function of the length of the probe used and of the degree of identity of the polynucleotides present in the library screened with this probe. It is necessary to adjust the hybridization conditions in order to optimize the signal generated by the homologous sequences which hybridize, while at the same time minimizing the background noise.

The polynucleotides capable of hybridizing selectively to the polynucleotides according to the invention may be isolated from genomic libraries or cDNA libraries produced, for example, from fungal strains, in particular strains of the *Penicillium* genus, for example the *P. funiculosum* IMI 134756 strain. The isolation of such polynucleotides may be carried out by standard hybridization techniques (Sambrook et al., 1989, Molecular Cloning: A Laboratory Manual, $2^{nd}$ edition, Nolan C. ed., New York: Cold Spring Harbor Laboratory Press), using, as a probe, a polynucleotide encoding the phytase represented by the sequence identifier SEQ ID NO: 3, a fragment of these polynucleotides, or a polynucleotide complementary thereto. When a polynucleotide has been isolated by these techniques, it is necessary to determine the sequence thereof and to identify the properties of the protein encoded by this polynucleotide, in particular to verify that this protein is a phytase equivalent to the phytase described by the sequence identifier SEQ ID NO: 3.

The hybridization techniques mentioned above therefore make it possible to isolate polynucleotides homologous to the polynucleotides encoding the phytase described by the sequence identifier SEQ ID NO: 3. Such polynucleotides, and the phytases which they encode, are readily identifiable by those skilled in the art in the biotechnology field who master standard molecular biology techniques. The invention therefore comprises polynucleotides homologous to the polynucleotides encoding the phytase described by the sequence identifier SEQ ID NO: 3. Advantageously, the degree of identity of the homologous polynucleotides will be at least 45% relative to the polynucleotides encoding the phytase represented by the sequence identifier SEQ ID NO: 3, preferably at least 50%, at least 70%, at least 80%, more preferentially at least 90%, and preferably at least 95%. The methods for measuring and identifying the degree of identity between sequences are well known to those skilled in the art. Use may be made, for example, of the programs PILEUP, BLAST (in particular Altschul et al., 1993, J. Mol. Evol. 36:290-300; Altschul et al., 1990, J. Mol. Biol. 215:403-10) or BestFit (Wisconsin Sequence Analysis Package, Version 8 for Unix, Genetics Computer Group, University Research Park, 575 Science Drive, Madison, Wis. 53711, using the algorithm of Smith and Waterman described in Applied Mathematics, 1981, No. 2, 482-489).

Such homologous polynucleotides may also be obtained artificially by conventional mutagenesis techniques.

A preferred polynucleotide encoding the phytase represented by the sequence identifier SEQ ID NO: 3 is selected from the sequences represented by the sequence identifiers SEQ ID NO: 1 and SEQ ID NO: 2.

By way of example of a homologous polynucleotide, mention may be made of the polynucleotide represented by the sequence identifier SEQ ID NO: 4.

According to a particular embodiment of the invention, the polynucleotides encoding a phytase, described above, originate from a fungus of the *Penicillium* genus. According to a particular embodiment, they originate from the *Penicillium* sp CBS 109899 strain or from the *Penicillium funiculosum* IMI 134756 strain.

According to a particular embodiment of the invention, the polynucleotides according to the invention encode a phytase having the following properties:

(a) optimum temperature=50° C.

(b) optimum pH=4-5

(c) Km=550 μm

The present invention also relates to fragments of the polynucleotides described above. The term "fragment" in particular denotes a fragment of at least 20 nucleotides, in particular at least 50 nucleotides, and preferably at least 100 nucleotides. Such fragments are generally designated oligonucleotides. They may be used as hybridization probes to identify homologous polynucleotides, or as prime-s to identify and amplify such homologous polynucleotides by the PCR (Polymerase Chain Reaction) technique as described in Ausubel et al., (1987) Current Protocols in Molecular Biology, edit. John Wiley & Sons, Section 6.3-6.4.

The term "fragment" also denotes fragments of the polynucleotides according to the invention encoding a fragment of the phytase represented by the sequence identifier SEQ ID NO: 3, or a fragment of a phytase homologous or equivalent to the phytase represented by the sequence identifier SEQ ID NO: 3.

The present invention also relates to polynucleotides comprising at least one of the polynucleotides as described above.

All the polynucleotides described above encode either the phytase represented by the sequence identifier SEQ ID NO: 3, or a homologous phytase, or an active fragment of these phytases. Consequently, the invention therefore extends to all the phytases encoded by all of these polynucleotides. This definition therefore includes the phytase represented by the sequence identifier SEQ ID NO: 3, the phytases homologous to this phytase, and the active fragments of these phytases.

According to a preferred embodiment of the invention, the phytase is a protein comprising at least the peptide sequence described by the sequence identifier SEQ ID NO: 3.

The invention therefore also comprises the phytases homologous to the phytase represented by the sequence identifier SEQ ID NO: 3. According to the invention, the term "homologous phytases" is intended to mean the phytases the sequences of which have modifications relative to the phytase represented by the sequence identifier SEQ ID NO: 3. Like the homologous polynucleotides, the homologous phytases are phytases the peptide sequences of which exhibit a certain degree of identity, which degree of identity is generally expressed by a percentage of identical amino acids. The invention therefore covers phytases which have one or more sequence modifications relative to the phytase represented by the sequence identifier SEQ ID NO: 3, and the properties of which are equivalent to those of the phytase described by the sequence identifier SEQ ID NO: 3. These modifications may be additions, deletions or substitutions of amino acids which may be natural or obtained by the usual mutagenesis techniques. Advantageously, the degree of identity of the homologous phytases will be at least 35% relative to the phytase represented by the sequence identifier SEQ ID NO: 3, preferably at least 50%, at least 70%, at least 80%, more preferentially at least 90%, and preferably at least 95%. The methods for measuring and identifying the degree of identity between the sequences are well known to those skilled in the art. Use may be made, for example, of the programs PILEUP, BLAST (in particular Altschul et al., 1993, J. Mol. Evol. 36:290-300; Altschul et al., 1990, J. Mol. Biol. 215:403-10) or BestFit (Wisconsin Sequence Analysis Package, Version 8 for Unix, Genetics Computer Group, University Research Park, 575 Science Drive, Madison, Wis. 53711, using the algorithm of Smith and Waterman described in Applied Mathematics, 1981, No. 2, 482-489).

By way of example of the phytase homologous to the phytase represented by the sequence identifier SEQ ID NO: 3, mention may be made of the phytase encoded by the polynucleotide represented by the sequence identifier SEQ ID NO: 4.

According to a particular embodiment of the invention, the phytase according to the invention originates from a fungus of the *Penicillium* genus.

According to a particular embodiment of the invention, the phytase has the following properties:

(a) optimum temperature=50° C.

(b) optimum pH=4-5

(c) Km=550 μm

The invention also extends to the fragments of the phytase represented by the sequence identifier SEQ ID NO: 3 and to the fragments of the homologous phytases. The term "fragment" is essentially intended to mean a biologically active fragment, i.e. a fragment having a phytase activity equivalent to that of the complete phytase, as measured by the assay described in example 2, or a similar assay.

The present invention also relates to a chimeric gene comprising, functionally linked to one another, at least one promoter which is functional in a host organism, a polynucleotide encoding a phytase according to the invention, and a terminator element that is functional in the same host organism. The various elements which a generic gene may contain are, firstly, elements regulating transcription, translation and maturation of proteins, such as a promoter, a sequence encoding a signal peptide or a transit peptide, or a terminator element constituting a polyadenylation signal and, secondly, a polynucleotide encoding a protein. The expression "functionally linked to one another" means that said elements of the chimeric gene are linked to one another in such a way that the function of one of these elements is affected by that of another. By way of example, a promoter is functionally linked to a coding sequence when it is capable of affecting the expression of said coding sequence. The construction of the chimeric gene according to the invention and the assembly of its various elements can be carried out using techniques well known to those skilled in the art, in particular those described in Sambrook et al. (1989, Molecular Cloning: A Laboratory Manual, Nolan C. ed., New York: Cold Spring Harbor Laboratory Press). The choice of the regulatory elements constituting the chimeric gene depends essentially on the host organism in which they must function, and those skilled in the art are capable of selecting regulatory elements which are functional in a given host organism. The term "functional" is intended to mean capable of functioning in a given host organism.

The promoters which the chimeric gene according to the invention may contain are either constitutive or inducible. By way of example, the promoters used for expression in bacteria may be chosen from the promoters mentioned below. For expression in *Escherichia coli* mention may be made of the lac, trp, lpp, phoA, recA, araBAD, prou, cst-l, tetA, cadA, nar, tac, trc, lpp-lac, Psyn, cspA, PL, PL-9G-50, PR-PL, T7, λPL-PT7, T3-lac, T5-lac, T4 gene 32, nprM-lac, VHb and the protein A promoters (Makrides, 1996, Microbiol. Rev. 60:512-538; Current Opinions in Biotechnology, 1996, 7; Weickert et al., 1996, Current Opinions in Biotechnology 7: 494-499) or else the $P_{trp}$ promoter (WO 99/64607). For expression in Gram-positive bacteria such as *Corynebacteria* or *Streptomyces*, mention may be made of the $P_{tipA}$ (Holmes et al., 1993, EMBO J. 12:3183-3191) or PS1 and PS2 (FR91/09870) promoters or those described in application EP0629699A2. For expression in yeasts and fungi, mention may be made of the *K. lactis* $P_{LAC4}$ promoters (Van den Berg et al., 1990, Bio/Technology 8:135-139) or the *K. lactis* $P_{pgk}$ promoter (patent application FR 91/05294), the *Trichoderma* tef1 or cbh1 promoter (WO 94/04673), the *Penicillium* his, csl or apf promoter (WO 00/68401) and the *Aspergillus* gla promoter (Gwynne et al., 1987, Bio/Technology 5:713-719).

The chimeric gene may also comprise a subcellular addressing sequence encoding a signal peptide or transit peptide. Such a sequence, located upstream or downstream of the polynucleotide encoding the phytase, makes it possible to direct said phytase specifically into a cellular compartment of the host organism, or to direct its secretion into the extracellular space. For example, the chimeric gene may comprise a sequence encoding a signal peptide or a transit peptide for directing the phytase toward a particular compartment of the cytoplasm, such as the mitochondria, the plasts, the endoplasmic reticulum or the vacuoles. Preferably, the addressing sequence encodes a signal peptide which addresses the phytase into the apoplast or the extracellular matrix.

According to one embodiment, the transit peptide may be a chloroplast, vacuolar or mitochondrial addressing signal which is then cleaved in the chloroplasts, the vacuoles or mitochondria. Such peptides are widely described in the literature: Neuhaus and Rodgers, 1998, Plant Molecular Biology 38: 127-144; EPSPS transit peptide described in patent U.S. Pat. No. 5,188,642; ribulose-biscarboxylase/oxygenase small subunit transit peptide (EP 189707).

According to another embodiment, the transit peptide may consist of a signal peptide for addressing into the bacterial periplasm, such as those of the pac (Schumacher et al., 1986, Nucl. Acids. Res. 14:5713-5727), ompA (Bowden and Georgiou, 1990, J. Biol. Chem. 265: 16761-16766) and phoA (Chang et al., 1986, Gene 44: 121-124) genes, or of a bacterial surface anchoring peptide, such as those of the PS1 and PS2 genes (FR91/09870).

The transit peptides may be single or double peptides. The double transit peptides are optionally separated by an intermediate sequence. By way of example of a chloroplast transit peptide, mention may be made of a double transit peptide comprising, in the direction of transcription, a sequence encoding a transit peptide of a plant gene encoding an enzyme located in plastids, a portion of sequence from the mature N-terminal portion of a plant gene encoding an enzyme located in plastids, and then a sequence encoding a second transit peptide of a plant gene encoding an enzyme located in plastids. Such double chloroplast transit peptides are, for example, described in patent application EP 0 508 909.

According to one embodiment, the transit peptide may be composed of various elements for increasing the amount of protein of interest secreted into the medium. Mention may thus be made of the combination of a carrier protein and a proteolytic cleavage site fused with the protein of interest (U.S. Pat. No. 6,130,063).

According to the invention, the chimeric gene may also comprise other regulatory sequences, which are located between the promoter and the coding sequence, such as transcription activators (enhancers).

The present invention also relates to a cloning, expression and/or transformation vector comprising a chimeric gene according to the invention. The vector according to the invention is of use for transforming a host organism and expressing in this organism a phytase. The vector may be a plasmid, a cosmid, a bacteriophage or a virus. Preferentially, the transformation vector according to the invention is a plasmid. Generally, the main qualities of this vector should be an ability to maintain itself and to self-replicate in the cells of the host organism, in particular by virtue of the presence of an origin of replication, and to express a phytase therein. For the purpose of stable transformation of the host organism, the vector may also integrate into the genome. The composition of the vector may then be limited to the elements required for synthesizing the phytase in the hosts. The choice of such a vector, and also the techniques of insertion of the chimeric gene according to the invention into this vector, are thoroughly described in Sambrook et al. (1989, Molecular Cloning: A Laboratory Manual, Nolan C. ed., New York: Cold Spring Harbor Laboratory Press) and are part of the general knowledge of those skilled in the art. Advantageously, the vector used in the present invention also contains, in addition to the chimeric gene according to the invention, a chimeric gene encoding a selectable marker. This selectable marker makes it possible to select the host organisms which are effectively transformed, i.e. those which incorporated the vector. Among the selectable markers which can be used, mention may be made of markers containing genes for resistance to antibiotics or to fungicides, such as, for example, the hygromycin phosphotransferase gene (Gritz et al., 1983, Gene 25: 179-188; Punt et al., 1987; Gene 56: 117-24), that of streptothricin acetyltransferase, that encoding a polypeptide conferring phleomycin resistance, that of mutated beta-tubulin conferring benomyl resistance (Gold et al., 1994, Gene 142: 225-30), or that of bialaphos acetyltransferase (Avalos et al., 1989, Curr Genet, 16:369-72). Other markers may be genes to complement an auxotrophy, such as the pyrA, pyrB, pyrG, pyr4 (Buxton and Radford, 1983, Mol. Gen. Genet. 190:403-405), arg4, argB (Berse et al., 1983, Gene 25:109-117) and trpC (Goosen et al., 1989, Mol. Gen. Genet., 219:282-88) genes, the molybdopterin synthase gene (Appleyard et al., 1998, J Biol Chem 273:14869-76; Unkles et al., 1999; J Biol Chem, 274:19286-93) or that of acetamidase (Beri and Turner, 1987, Curr Genet, 11:639-41). Another category of selectable markers consists of genes for tolerance to herbicides, such as the bar gene (White et al., NAR 18:1062, 1990) for bialaphos tolerance, the EPSPS gene (U.S. Pat. No. 5,188,642) for glyphosate tolerance, the HPPD gene (WO 96/38567) for isoxazole tolerance, or the glyphosate oxydoreductase gene (U.S. Pat. No. 5,463,175). Mention may also be made of genes encoding readily identifiable enzymes such as the GUS enzyme, or genes encoding pigments or enzymes regulating the production of pigments in the transformed cells. Such selectable marker genes are in particular described in patent applications WO 91/02071, WO 95/06128, WO 96/38567 and WO 97/04103.

The present invention also relates to transformed host organisms containing at least one chimeric gene according to the invention, either integrated into their genome or carried on an extrachromosomal genetic element, for example a plasmid. The term "host organism" is intended to mean any lower or higher monocellular or pluricellular organism into which the chimeric gene according to the invention may be introduced in order to produce a phytase according to the invention. Preferably, the host organism is a microorganism, in particular a fungus, for example of the *Penicillium, Aspergillus, Chrysosporium* or *Trichoderma* genus, a bacterium, for example of the *Escherichia* genus, in particular *E. coli*, of the *Corynebacterium* genus, of the *Bacillus* genus or of the *Streptomyces* genus, a yeast, in particular of the *Saccharomyces, Kluyveromyces* or the *Pichia* genus, a baculovirus, or plant cells. The host organism may also be a plant or a part of a plant.

The expression "transformed host organism" is intended to mean a host organism which has incorporated into its genome, or in an extrachromosomal genetic element, for example a plasmid, at least one chimeric gene according to the invention, and consequently produces a phytase in its tissues, or in a culture medium. To obtain the host organisms according to the invention, those skilled in the art may use one of the many known transformation methods.

One of these methods consists in bringing the cells or tissues of the host organisms to be transformed into contact with polyethylene glycol (PEG) and with the vectors according to the invention (Chang and Cohen, 1979, Mol. Gen. Genet. 168(1), 111-115; Mercenier and Chassy, 1988, Biochimie 70(4), 503-517). Electroporation is another method, which consists in subjecting the cells or tissues to be transformed and the vectors of the invention to an electric field (Andreason and Evans, 1988, Biotechniques 6(7), 650-660; Shigekawa and Dower, 1989, Aust. J. Biotechnol. 3(1), 56-62). Another method consists in directly injecting the vectors into the cells or the tissues by microinjection (Gordon and Ruddle, 1985, Gene 33(2), 121-136). Advantageously, the "biolistic" method may be used. It consists in bombarding cells or tissues with particles onto which the vectors of the invention are adsorbed (Bruce et al., 1989, Proc. Natl. Acad. Sci. USA 86(24), 9692-9696; Klein et al., 1992, Biotechnology 10(3), 286-291; U.S. Pat. No. 4,945,050).

Several methods for transforming bacteria are described in the literature for *Escherichia coli* and other Gram-negative bacteria (Ausubel et al., 1995, Current Protocols in Molecular Biology, John Wiley and Sons, New York; Inoue et al., 1990, Gene 96: 23-28; Chung et al., 1989, Proc. Natl. Acad. Sci. USA 86: 2172-2175). Conjugation may also be used (Cameron et al., 1989, J. Bacteriol., 171: 547-557). For Gram-positive bacteria, electroporation may be used, and also protoplast transformation, in particular for bacteria of the *Streptomyces* genus (Bonamy et al., 1990, FEMS Microbio. Lett 66: 263-270; Hopwood et al., 1985, Genetic Manipulation of *Streptomyces*: A Laboratory Manual. John Innes Foundation, Norwich).

Several methods for transforming fungi are also described in the literature (Talbot, 2001, Molecular and cellular biology of filamentous fungi, Oxford University Press, New York). Protoplast transformation with PEG is described for *Aspergillus* in EP 0260762, and an adaptation of this method to the species *Penicillium funiculosum* is described in WO 00/36120. Transformation by restriction enzyme mediated integration, or REMI (Sanchez et al., 1998, Mol. Gen. Genet. 258; 89-94), is also known, as is protoplast transformation using bacteria of the *Agrobacterium* genus (de Groot et al., 1998, Nature Biotechnology 16: 839-842). Techniques for transforming yeasts are also described in the literature, in particular in Ausubel et al. (1995, Current Protocols in Molecular Biology, John Wiley and Sons, New York) and Van den Berg et al. (1990, Bio/Technology 8: 135-139).

In the particular case when the host organism to be transformed is of plant origin, the plant cells or tissues may preferentially be transformed using bacteria of the *Agrobacterium* genus, preferably by infection of the cells or tissues of said plants with *A. tumefaciens* (Knopf, 1979, Subcell. Biochem. 6, 143-173; Shaw et al., 1983, Gene 23-(3):315-330) or *A. rhizogenes* (Bevan and Chilton, 1982, Annu. Rev. Genet. 16:357-384; Tepfer and Casse-Delbart, 1987, Microbiol. Sci. 4(1), 24-28). Preferentially, the transformation of plant cells or tissues with *Agrobacterium tumefaciens* is carried out according to the protocol described by Ishida et al. (1996, Nat. Biotechnol. 14(6), 745-750). Those skilled in the art will choose the appropriate method depending on the nature of the host organisms to be transformed.

The present invention also relates to a method for producing an extract having phytase activity. According to one embodiment of the invention, this method comprises the steps of:
(a) culturing an organism which naturally possesses a polynucleotide according to the invention in its genome, under conditions which allow it to express said phytase
(b) concentrating the organism cultured in step (a)
(c) rupturing the cells of the organism isolated in step (b)
(d) centrifuging the ruptured cellular extract obtained in step (c)
(e) recovering the supernatant having the phytase activity, derived from step (d).

Step (c) may be carried out using techniques known to those skilled in the art, such as mechanical grinding (by pressure difference, by ultrasound action, by trituration), enzymatic lysis or osmotic shock, said techniques possibly being used individually or in combination.

The present method may also become a method for producing a phytase according to the invention by adding an additional step (f) of purification. The step (f) of such a method for producing a phytase according to the invention consists in purifying the phytase from the supernatant recovered in step (e). The purification of the phytase may be carried out by any technique for concentrating or separating proteins, in particular the techniques of microfiltration, ultrafiltration, electrophoresis or chromatography, well known to those skilled in the art. In order to obtain a purified phytase, those skilled in the art may be able to use the abovementioned method for measuring the phytase activity in order to identify the purification fraction(s) containing said phytase. According to this method, the phytase produced may have a purity of preferably 50%, 60%, 70%, 80%, 90%, 95%, 99%, or advantageously 100%.

According to another embodiment of the method according to the invention, in particular when the phytase according to the invention is secreted into the culture medium, said method comprises the steps of:
(a) culturing an organism which possesses a polynucleotide according to the invention, under conditions which allow it to express said phytase
(b) recovering the culture medium by removing said organism.

The expression "organism which naturally possesses a polynucleotide according to the invention in its genome" is intended to mean any organism which, in the natural state, possesses a polynucleotide encoding a phytase described by the sequence identifier SEQ ID NO: 3 or a homologous polynucleotide in its genome.

According to one embodiment of the methods described above, said organism is a microorganism. According to a particular embodiment, said microorganism is a fungus, in particular a fungus of the *Penicillium* genus, in particular the *Penicillium* sp CBS 109899 strain, which was deposited on Nov. 28, 2001, as Accession No. CBS 109899 at the International Depository Authority Centraalbureau voor Schimmelcultures, Uppsalalaan 8, P.O. Box 85167, 3508 AD UTRECHT, The Netherlands.

According to these methods, the organism is cultured in a medium suitable for the production of a phytase using the techniques known to those skilled in the art. Said organism, in particular when it is a microorganism, in particular a fungus, may be cultured in a shaken Erlenmeyer flask, a laboratory-scale fermentor or an industrial-scale fermentor (batch fermentation, fed-batch fermentation or fermentation under solid medium). The culture medium used should contain sources of carbon and nitrogen and inorganic salts. In the particular embodiment of the method using the *Penicillium* sp CBS 109899 strain as the organism, the expression of the phytase is obtained in the presence or absence of phytate salts (by way of example, the phytate salts may be Nag salts, $Ca^{++}$ salts or a combination of $Ca^{++}$ and $Mg^{++}$ salts). The pH may be controlled (pH 3 or 4 preferably) or left free.

According to this method, the step of recovering the culture medium by removal of said organism may be carried out by any means for separating solid fractions included in a liquid fraction. In particular, filtration and centrifugation are suitable means for carrying out this step.

The present method may also become a method for producing a phytase according to the invention by adding an additional step (c) of purification. Step (c) of such a method for producing a phytase according to the invention consists in purifying the phytase from the supernatant recovered in step (b). The phytase may be purified by any technique for concentrating or separating the proteins, in particular the techniques of microfiltration, of ultrafiltration, of electrophoresis or chromatography, well known to those skilled in the art. In order to obtain a purified phytase, those skilled in the art will be able to use the abovementioned method for measuring the phytase activity in order to identify the purification fraction(s) containing said phytase. According to this method, the phytase produced may have a purity of preferably 50%, 60%, 70%, 80%, 90%, 95%, 99%, or advantageously 100%.

According to another embodiment of the invention, the method for producing an extract having phytase activity uses a trans-formed host organism according to the invention, and comprises the steps of:

(a) culturing a transformed host organism according to the invention (b) concentrating the transformed host organism cultured in step (a)

(c) rupturing the cells of the organism isolated in step (b)

(d) centrifuging the ruptured cellular extract obtained in step (c)

(e) recovering the supernatant having the phytase activity, derived from step (d).

Step (c) may be carried out using techniques known to those skilled in the art, such as mechanical grinding (by pressure difference, by ultrasound action, by trituration), enzymatic lysis or osmotic shock, said techniques possibly being used individually or in combination.

The present method may also become a method for producing a phytase according to the invention by adding an additional step (f) of purification. The step (f) of such a method for producing a phytase according to the invention consists in purifying the phytase from the supernatant recovered in step (e). The purification of the phytase may be carried out by any technique for concentrating or separating proteins, in particular the techniques of microfiltration, ultrafiltration, electrophoresis or chromatography, well known to those skilled in the art. In order to obtain purified phytase, those skilled in the art will be able to use the abovementioned method for measuring the phytase activity in order to identify the purification fraction(s) containing said phytase. According to this method, the phytase produced may have a purity of preferably 50%, 60%, 70%, 80%, 90%, 95%, 99%, or advantageously 100%.

Preferably, the transformed host organism used in this method is a microorganism. In particular, said microorganism may be a fungus, for example of the *Penicillium, Aspergillus, Chrysosporium* or *Trichoderma* genus, a bacterium, for example of the *Escherichia* genus, in particular *E. coli*, of the *Corynebacterium* genus, of the *Bacillus* genus or of the *Streptomyces* genus, a yeast, in particular of the *Saccharomyces, Kluyveromyces* or *Pichia* genus, a baculovirus, or plant cells.

According to another embodiment of the invention, in particular when the phytase according to the invention is secreted into a culture medium, this method comprises the steps of:

(a) culturing a transformed host organism according to the invention (b) recovering the culture medium by removing said transformed host organism.

According to these methods, the organism is cultured in a medium suitable for the production of a phytase using the techniques known to those skilled in the art. Said organism, in particular when it is a microorganism, in particular a fungus, may be cultured in a shaken Erlenmeyer flask, a laboratory-scale fermentor or an industrial-scale fermentor (batch fermentation, fed-batch fermentation or fermentation on solid medium). The culture medium used should contain sources of carbon and nitrogen and inorganic salts.

According to this method, the step of recovering the culture medium by removing the transformed host organism may be carried out by any means for separating solid fractions included in a liquid fraction. In particular, filtration and centrifugation are suitable means for carrying out this step.

The present method may also become a method for producing a phytase according to the invention by adding a further step (c) of purification. Step (c) of such a method for producing a phytase according to the invention consists in purifying the phytase from the supernatant recovered in step (b). The phytase may be purified by any technique for concentrating or separating proteins, in particular the techniques of microfiltration, of ultrafiltration, of electrophoresis or of chromatography, well known to those skilled in the art. In order to obtain a purified phytase, those skilled in the art will be able to use the abovementioned method for measuring the phytase activity in order to identify the purification fraction(s) containing said phytase. According to this method, the phytase produced may have a purity of preferably 50%, 60%, 70%, 80%, 90%, 95%, 99%, or advantageously 100%.

The present invention, also relates to enzymatic compositions comprising at least one phytase according to the invention.

The term "enzymatic composition" is intended to mean a composition comprising at least one phytase according to the invention, which phytase may be in varying proportions depending on whether or not it is combined with diverse adjuvants promoting its stability and its conservation. By way of examples of adjuvants which may be used in an enzymatic composition according to the invention, mention may be made of sorbitol, mannitol, benzoate, inorganic salts, or plant oils. The enzymatic composition according to the invention may be in liquid form, said composition and the phytase which it contains then being in an aqueous solution, or in solid form, said composition and the phytase which it contains then being lyophilized in the form of a powder.

According to a particular embodiment of the invention, the enzymatic composition comprises, in addition to the phytase according to the invention, at least one additional enzyme. This additional enzyme may either have phytase activity or have an activity other than phytase activity. When this additional enzyme has phytase activity, said phytase activity is preferably different from and complementary to the phytase activity of the phytase according to the invention. When this additional enzyme has an activity other than phytase activity, it may, for example, have xylanase, cellulase, β-glucanase, laminarinase, ferulic acid esterase, pullulanase, protease, amidase, phosphatase or mannanase activity.

Preferably, said enzymatic compositions are intended to be incorporated into feedstuffs for livestock animals, in particular monogastric animals, preferably pigs or poultry.

The present invention also relates to a feed composition comprising at least one phytase according to the invention.

The term "feed composition" is essentially intended to mean a feedstuff intended for livestock animals, in particular for monogastric animals, preferably pigs or poultry. A feed composition according to the invention is ideally a feedstuff intended for livestock animals, supplemented with an enzymatic composition according to the invention. The feed composition according to the invention is therefore a feedstuff for livestock animals, to which at least one enzymatic composition according to the invention is added, said feedstuff and said enzymatic composition being mixed so as to obtain said feed composition.

According to a particular embodiment of the invention, said feed compositions comprise at least one transformed host organism according to the invention. According to another particular embodiment of the invention, said feed compositions comprise at least one organism which possesses a polynucleotide according to the invention, in particular at least one fungus of the *Penicillium* genus, in particular fungus of the *Penicillium* sp CBS 109899 strain.

Advantageously, the feed compositions according to the invention are intended to be used in monogastric animal nutrition. According to a particular embodiment of the invention, said feed compositions are intended for pig nutrition. According to another particular embodiment of the invention, said feed compositions are intended for poultry nutrition.

The subject of the present invention is also a method for producing a feed composition as described above.

According to a particular embodiment of the invention, said method consists in culturing a host organism according to the invention or an organism which possesses a polynucleotide according to the invention, in particular a fungus, more precisely a fungus of the *Penicillium* genus, in particular the *Penicillium* sp CBS 109899 strain, in concentrating said organisms by any concentration method known to those skilled in the art, in particular filtration or centrifugation, and then in incorporating said concentrated organisms into a feed composition.

According to another particular embodiment of the invention, said method consists in producing an extract having phytase activity or a phytase according to the invention by one of the methods for producing said extract or said phytase, as described above, and then in incorporating said extract or said phytase produced into a feed composition.

The present invention also relates to a method for increasing the assimilation of the inorganic phosphate contained in the phytate of plant-based feedstuffs by monogastric animals, wherein a phytase or an enzymatic composition according to the invention is incorporated into the nutrition of said animals. Preferably, in said method, said monogastric animals are fed with a feed composition according to the invention.

The invention also relates to a method for decreasing the addition of phosphorus in monogastric animal nutrition, wherein said animals are fed with a feed composition according to the invention.

The invention also relates to a method for decreasing the discharge of phosphorus derived from monogastric animal nutrition, wherein said animals are fed with a feed composition according to the invention.

The present invention also relates to a filamentous fungus of the *Penicillium* sp. genus having the deposit number CBS 109899.

The examples below make it possible to illustrate the present invention without, however, limiting the scope thereof.

EXAMPLE 1

Characteristics and Culturing of the *Penicillium* sp. CBS 109899 Strain 1.1. Characteristics On PDA agar medium (24 g/l potato dextrose broth, 16 g/l agar-agar), the mycelium of the CBS 109899 strain develops at 30° C. and, upon aging, is yellow in color. The aerial mycelium is observed at the periphery of the column, without the characteristic structures of *Penicillium*. After culturing the fungus in MN-Uri liquid medium (P. J. Punt, and C. A. M. J. J. van den Bondel, (1992) Methods in Enzymology 216, 447-457) at 28° C., for 2 days with shaking, the mycelium was recovered by filtration and ground in liquid nitrogen. Extraction of the genomic DNA is carried out by the phenol-chloroform method well known to those skilled in the art, on 1 g of ground material in 5 ml of lysis buffer (1% SDS, 2% Triton X-100, 100 mM NaCl, 1 mM EDTA, 10 mM Tris, pH 8.0). After purification, the genomic DNA was precipitated by adding 2 volumes of ethanol. A PCR amplification carried out with a high fidelity polymerase and with the primers PN3 (SEQ ID NO:5) and PN4 (SEQ ID NO: 6) made it possible to obtain a 1175 bp fragment which was sequenced (SEQ ID NO:7).

PN3: 5'-CCGTTGGTAACCAGCGGAGGGATC-3'

PN4: 5'-CCTTGGTCCGTGTTTCAAGACGGG-3'

Alignment of this internal transcribed spacer sequence with the ITS sequences available in the databanks shows a 96% identity with the ITS sequence identified as that of a *Penicillium aculeatum* and 96% identity with the ITS sequence of *Penicillium funiculosum* IMI 134756. The CBS 109899 strain was therefore named *Penicillium* sp.

1.2. Culturing Conditions

A synthetic medium for culturing the CBS 109899 strain was determined. It is composed of 10 g/l glucose, 0.1 M $NH_4NO_3$, 1.5 g/l $KH_2PO_4$, 0.5 g/l KCl, 0.5 g/l $MgSO_4$, 10 mg/l $MnCl_2$, 10 mg/l $ZnSO_4$ and 10 mg/l $FeSO_4$ in demineralized water. For expression of the phytase, a 1 $cm^2$ mycelium sample taken from a colony having grown on a PDA medium is incubated in 30 ml of MSP3 medium (10 g/l glucose, $NaNO_3$, 20 g/l calcium phytate, 0.5 g/l KCl, 0.5 g/l $MgSO_4$, 2.2 mg/l $ZnSO_4$, 1.1 mg/l $H_3BO_3$, 0.5 mg/l $MnCl_2$, 0.5 mg/l $FeSO_4$, 0.17 mg/l $CaCl_2$, 0.16 mg/l $CuSO_4$, 0.15 mg/l $Na_2MoO_4$ and 5 mg/l $Na_2EDTA$) for 7 days at 30° C. with shaking. The culture is centrifuged for 10 minutes at 5000 rpm and the supernatant is analyzed as described in example 2.

EXAMPLE 2

Measurement of Phytase Activity

The measurement of phytase activity is based on the method of Shimizu (1992, Biosci. Biotech. Biochem. 56(8), 1266-1269). The principle of this method consists in measuring the amount of inorganic phosphate released during the enzymatic reaction of the phytase with its substrate (solution of sodium phytate prepared at 10 g/l in a 250 mM acetate buffer containing 1 mM $CaCl_2$, pH 5.5). The amount of inorganic phosphate released is measured by reaction of this phosphate with a chromogenic reagent (1 volume of iron sulfate at 10.8% mixed extemporaneously with 4 volumes of ammonium molybdate at 0.012M $H_2SO_4$). This reaction leads, in highly acidic medium, to the formation of a colored phosphomolybdate complex (in the presence of $Fe^{2+}$), and the amount of complex formed is quantified by measuring the absorbance at 700 nm of the colored solution generated, on a spectrophotometer.

Three reactions are carried out in parallel in order to produce enzymatic kinetics at 10, 20 and 30 minutes at 37° C. The enzymatic reactions are stopped by adding 2.5 ml of 20% trichloroacetic acid. The sample interference is determined by adding the 20% trichloroacetic acid and then the phytic acid to the crude extract, which may or may not be diluted. The blank for the enzymatic reaction is prepared with 250 mM of acetate buffer containing 1 mM $CaCl_2$, pH 5.5. After the reactions have been stopped, the amount of phosphate released is revealed by adding the same volume of colored reagent [1 volume of $FeSO_4.7H2O$+4 volumes of ammonium heptamolybdate solution]. The intensity of the blue coloration is measured by spectrophotometry at 700 nm. It is related to the phosphate concentration using a $KH_2PO_4$ range of between 0 and 1 mM. The enzymatic activity is determined using the rate of appearance of the phosphate in the course of the enzymatic kinetics.

EXAMPLE 3

Isolation of a Fungal Extract Containing Phytase Activity

The CBS 109899 strain is cultured on the scale of an Erlenmeyer flask, and in fermentors of 3 to 200 liters at 30° C. for 6 to 8 days. The production medium is composed of 10 g/l glucose, 40 g/l starch, 25 g/l rice bran, 20 g/l $Ca^{2+}$ phytate, 15 g/l ammonium chloride, 0.5 g/l ammonium sulfate and 0.9 g/l antifoaming agent. The pH is adjusted to 5.5, but it is not controlled during fermentation. A 4% inoculum is used to start the fermentations. This inoculum corresponds to a culture of 3 to 4 days at 30° C., composed of 10 g/l glucose, 10 g/l peptone, 5 g/l Na-CMC, 0.5 g/l magnesium sulfate, 0.5 g/l calcium chloride, 0.01 g/l $FeSO_4.7H_2O$ and 0.01 g/l $MnSO_4.4H_2O$. The inoculum is directly seeded with spores or a piece of agar (PDA medium, 10 days at 30° C.) on which the fungus is cultured. It may also itself be seeded with a 3- to 4-day culture prepared under the same conditions.

At the end of fermentation, the entire culture is filtered and the filtrate is concentrated by ultrafiltration through an organic or inorganic membrane with a cutoff of 10 kDa. The activity is determined on a sample of the ultrafiltration retentate and is related to the initial fermentation volume (Table 1).

Table 1: Activities Obtained at the End of Fermentation as a Function of the Fermentation Volume

| Fermenter volume | Agitation rpm | Aeration vvm | Activity U/mL |
|---|---|---|---|
| Erlenmeyer flask | 220 | — | 45-63 |
| 3 L | 450 | 1 | 45 |
| 30 L | 400 | 1 | 55-66 |

EXAMPLE 4

Characteristics of the Isolated Phytases According to the Invention

The optimum pH and optimum temperature, the stabilities to pH and temperature and also the Michaelis constants of the crude fungal extract provided were determined using the method described in example 2.

4.1. Michaelis Constants

The Michaelis-Menten constant ($Km_{app}$) and the maximum reaction rate ($Vm_{app}$) were obtained by modifying the substrate concentrations and the incubation times. The phytase contained in the fungal extract is characterized by a $Km_{app}$ of 550 μM and a $Vm_{app}$ of 1.425 μmol of phosphate released per minute and per mg of sample.

4.2. Phytase Activity as a Function of pH

The optimum pH was measured by modifying the pH and/or the nature of the reaction buffer (at pH 2: KCl-HCl buffer; at pH 3: glycine-HCl buffer; at pH 4, 5, 5.5 and 6: sodium acetate buffer; at pH 7: Tris-HCl buffer). The results given in FIG. 1 show the relative activity calculated with respect to the maximum enzymatic activity obtained. The optimum pH of the phytase contained in the fungal extract, measured at 37° C., is between pH 4 and pH 5.

4.3. Phytase Activity as a Function of Temperature

Figure 2:
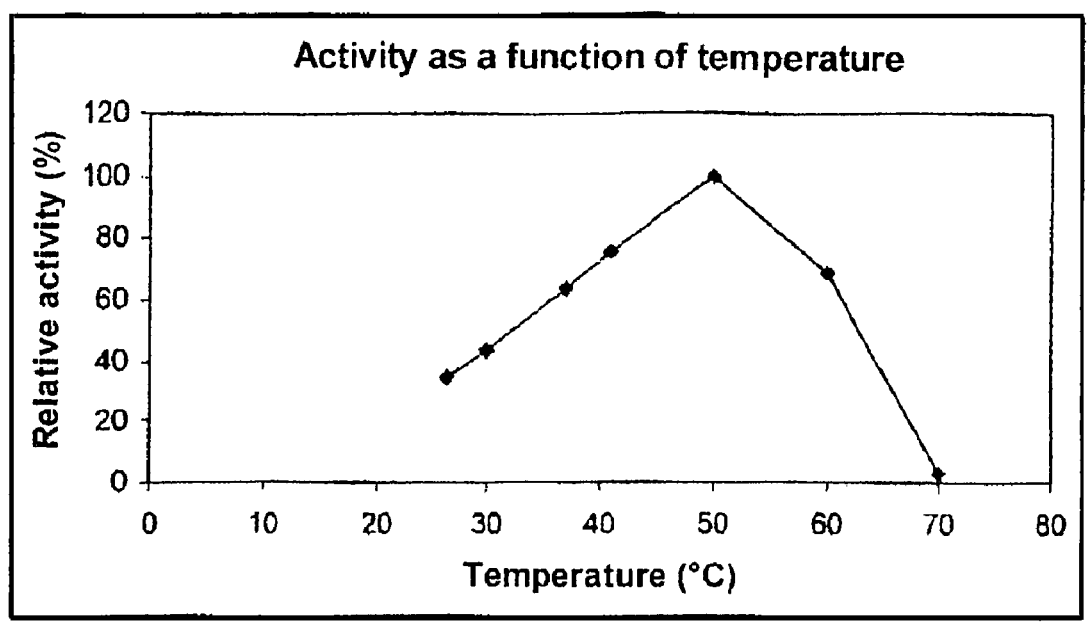
FIG. 2: Activity of the phytase of *Penicillium* sp CBS 109899 as a function of temperature. The value 100% of relative activity corresponds to the optimum activity of the phytase for a given temperature.

The optimum temperature was measured by modifying the incubation temperature for the enzymatic reactions. The data obtained, given in FIG. 2, show the relative activity calculated with respect to the maximum enzymatic activity determined. The optimum temperature of the phytase contained in the fungal extract, at pH 5.5, is in the region of 50° C.

4.4. Stability of the Phytase as a Function of pH

The resistance of the phytase activity to acid pHs was evaluated. After exposure of the extract to pHs of between pH 2 and pH 6.5 at 41° C., for 0 to 180 minutes, the pH of the solutions is stabilized at pH 5.5 by dilution. The activity is then determined by the method described in example 2. The results show that the phytase activity of the extract is relatively stable down to a pH of 3.5. However, it is rapidly denatured at more acid pHs, in particular at pH 2.

4.5. Stability of the Phytase as a Function of Temperature

The thermostability of the phytase activity was evaluated for temperatures greater than or equal to 60° C. A dilute solution (final concentration 1 IU/ml) of the extract is brought to the test temperature for a given amount of time (not exceeding 30 minutes). After returning to ambient temperature, each heat-treated solution is assayed according to the method described in Example 2. From 5 minutes at 60° C., the phytase activity is decreased by approximately 80% until it is virtually zero after 1 minute at 80° C. under the conditions for carrying out the experiments.

EXAMPLE 5

Purification of a Phytase According to the Invention

A fungal enzymatic extract as obtained in example 3 was concentrated by ultrafiltration using a membrane with a cutoff of 10 kDa. The ionic strength and the pH of the extract are adjusted by several washes with a 20 mM glycine buffer, pH 3.

Cation exchange chromatography is carried out by applying the concentrate obtained to an SP10 column (PerSeptive BioSystems), at a stationary pH of 3. The proteins attached are eluted with a step gradient of 0 to 1M NaCl in glycine buffer at a flow rate of 3 ml/min. A peak of phytase activity is obtained for approximately 30% of 1M NaCl. The phytase is separated from the other components of the activity peak by gel permeation on an HR200 column (Pharmacia) in 50 mM sodium acetate buffer, pH 5.5, at a flow rate of 0.7 ml/min. The purity of the fractions collected is estimated by nondenaturing polyacrylamide gel electrophoresis with silver staining. A single protein band is present on the gel, with an estimated molecular weight of 130 kDa. However, after SDS-PAGE electrophoresis of the purified phytase, 2 polypeptide bands were observed, one being a major band at a relative migration distance of 70 kDa, the other being a minor band at a relative migration distance of 90 kDa.

EXAMPLE 6

Microsequencing of the Purified Phytase 6.1. Determination of the N-Terminal Sequence The polypeptides corresponding to the polypeptide bands of 70 and 90 kDa obtained by SDS-PAGE electrophoresis were transferred onto a PVDF membrane (ProBlott, Applied Biosystems) for 15 h at 4° C. The polypeptides were detected by staining with amido black 10B (Sigma) and subjected to sequencing (Institut Pasteur, Laboratoire de Microséquencage des Protéines [Protein Microsequencing Laboratory], Paris). The same N-terminal sequence was obtained for the two polypeptide bands (SEQ ID NO:8).

This result led to the conclusion that the two polypeptide bands identified on SDS-PAGE probably corresponded to the same polypeptide, the difference in migration rate possibly resulting from partial degradation of a fraction of the polypeptide during the purification steps.

6.2. Determination of the Amino Acid Sequence of Internal Fragments of the Phytase The 2 polypeptides of 70 and 90 kDa were separated by SDS-PAGE electrophoresis and detected by staining with amido black. The polypeptide band at 70 kDa was excised from the gel and the polypeptide was subjected to digestion in situ with Endolysine-C for 18 h at 37° C. The peptide fragments were separated by HPLC on a C18 DEAE column. The sequences of 4 internal fragments were obtained by microsequencing (SEQ ID NO: 9, SEQ ID NO: 10, SEQ ID NO: 11 and SEQ ID NO: 12).

SEQ ID NO: 8: IPTDPQVPQ/VYF

SEQ ID NO: 9: TSGGDAVNEWTALYLQK

SEQ ID NO: 10: AGGAPFLAQXNPIYXQPXYV

SEQ ID NO: 11: LYDPASK

SEQ ID NO: 12: APGLVR

EXAMPLE 7

Production of a Molecular Probe Relating to the Phytase of *Penicillium* sp. CBS 109899

After microsequencing, oligonucleotides were deduced from the peptides in order to amplify, by PCR, a DNA fragment relating to the gene encoding the phytase of *Penicillium* sp. CBS 109899.

7.1. PCR Primer Design

Primers were deduced from the N-terminal amino acid sequence of the internal sequence SEQ ID NO: 9. The sequence of the N-terminal end led to the deduction of 4 pools of sense degenerate primers, and the internal sequence SEQ ID NO: 9 led to the deduction of 1 pool of reverse degenerate primers. Each of the pools of sense primers was used separately with the pool of reverse primers.

7.2. Amplification of a Genomic DNA Fragment Relating to the Phytase

First, *Penicillium* sp. CBS 109899 was cultured in liquid MN-Uri medium (28° C., 180 rpm, 2 days). The mycelium was recovered by filtration, and ground in liquid nitrogen. The extraction of the genomic DNA was carried out in 5 ml of lysis buffer (1% SDS, 2% Triton X-100, 100 mM NaCl, 1 mM EDTA and 10 mM Tris, pH 8.0) and 5 ml of phenol on 1 g of ground material. After purification of the aqueous phase by phenol/chloroform and chloroform extraction, the genomic DNA was precipitated by adding 2 volumes of ethanol.

The PCR reactions were carried out on 100 ng of genomic DNA with 1 unit of Taq polymerase (Q-BIOgene) and using an MJ Research thermal cycler model PTC-200. The reaction product from each PCR was analyzed on 0.8% agarose gel. A nucleotide fragment in the region of 850 bp and corresponding to the pair of primers OT ACS 17 P4.4 (SEQ ID NO: 13) and OT ACS 25 P6.1 (SEQ ID NO: 14) was obtained, directly subcloned into the vector pCR4-TOPO (Invitrogen) and sequenced (SEQ ID NO: 15).

Analysis of the sequence showed that the two primers used for the amplification were present on either side of the amplified fragment and that the deduced amino acid sequences following on from them were coherent with those obtained by microsequencing the phytase. Furthermore, the amino acid sequences of the internal peptide fragments SEQ ID NO: 10 and SEQ ID NO: 11 appeared within the amino acid sequence deduced from the DNA fragment. These observations led to the conclusion that the amplified DNA fragment corresponded to the microsequenced phytase, and it was named OT ACS 29.1. This DNA fragment was then used as a homologous molecular probe to clone the gene encoding the purified phytase.

OT ACS 17 P4.4 (SEQ ID NO: 13) 5'-ACNGAYCCN-CARGTCCC

OT ACS 25 P6.1 (SEQ ID NO: 14) 5'-GCNGTCCAYT-CRTTNAC

EXAMPLE 8

Cloning and Characterization of the Gene Encoding the Phytase of *Penicillium* sp. CBS 109899

8.1. Determination of the Sequence of the cDNA Relating to the Phytase

The complete sequence of the cDNA was obtained by amplification, subcloning and sequencing of its 5' and 3' ends according to the 5' and 3' RACE-PCR technique.

First, *Penicillium* sp. CBS 109899 was cultured under conditions of induction for the phytase in a medium composed of 40 g/l of starch flour, 25 g/l rice bran, 20 g/l calcium phytate, 10 g/l glucose, 15 g/l $NH_4Cl$ and 0.5 g/l $MgSO_4.7H_2O$, pH 5.5, and supplemented with 0.06 g/l glucoamylase AMG 300 L (Novozymes) and 0.18 g/l alpha amylase Termamyl 120 L (Novozymes). The culture was allowed to continue until a phytase activity of 10 U/ml of culture medium was attained. The mycelium was recovered by filtering the culture through filter paper (Whatman), and then ground in liquid nitrogen. The total RNA was extracted from the ground material by phenol extraction in a 50 mM sodium acetate buffer, pH 5.3, containing 10 mM EDTA. The mRNAs were then reverse transcribed using the GeneRacer kit (Invitrogen). The cDNAs synthesized had a given nucleotide sequence at their 5' and 3' ends, for subsequent PCR amplification. In order to amplify specifically the ends of the cDNA of interest, 2 primers, one oriented toward the 5' end, named OT ACS 37 P1 (SEQ ID NO: 20), the other toward the 3' end, named OT ACS 37 P3 (SEQ ID NO: 21), were deduced from the molecular probe in a region relating to the peptide sequence SEQ ID NO: 10.

The PCR reactions were carried out on 1 µl of cDNA synthesis product with 1 unit of Taq polymerase (Q-BIOgene) using an MJ Research thermal cycler model PTC-200. The amplification products were analyzed on 0.8% agarose gel. A fragment in the region of 0.3 kb relating to the 5' end and another in the region of 1.7 kb relating to the 3' end were directly subcloned into the vector pCR4-TOPO (Invitrogen), and then sequenced. The sequence of the complete cDNA was then reconstituted (SEQ ID NO: 2).

OT ACS 37 P1 (SEQ ID NO: 20) 5'-GGCGCTCCGTTCCTTGCGCAAAC-3'

OT ACS 37 P3 (SEQ ID NO: 21) 5'-GTAGGTCGGCTGGGAATAGATCG-3'

8.2. Subcloning of an EcoRV Genomic DNA Fragment Containing the Gene

A fragment of genomic DNA was cloned using the genome walking technique. First, an adapter was ligated to the ends of the EcoRV restriction fragment. To do this, the product of EcoRV digestion of the genomic DNA of *Penicillium* sp. CBS 109899 was ligated to a GenomeWalker Adaptor (CLONTECH Laboratory, Inc) with T4 DNA ligase in a 50 mM Tris-HCl buffer, pH 7.5, containing 10 mM $MgCl_2$, 10 mM dithiothreitol, 1 mM ATP and 0.25 µg/ml of bovine serum albumin, for 15 h at 16° C. The reaction was stopped by heat treatment at 70° C. and the reaction mixture was taken up in 200 µl of ultrapure water.

In order to amplify, by PCR, the 5' and 3' regions of the EcoRV restriction fragment, two sense primers were deduced from the molecular probe, one oriented toward the 5' end, named OT ACS 32 P5 (SEQ ID NO: 16), the other toward the 3' end, named OT ACS 32 P3 (SEQ ID NO: 17). The reverse primer, named Adaptor Primer (CLONTECH Laboratory, Inc), used for the PCR reactions corresponded to the sequence of the 5' end of the adapter.

The PCR reactions were carried out on 1 µl of the ligation product with 1 unit of Advantage Genomic Polymerase Mix (CLONTECH Laboratory, Inc) and using an MJ Research thermal cycler model PTC-200. The reaction product from each PCR was analyzed on 0.8% agarose gel.

Two fragments, one in the region of 1.8 kb relating to the 5' end, and the other in the region of 1.3 kb relating to the 3' end, were subcloned and analyzed by sequencing. Once the 5' and 3' nucleotide sequences of the EcoRV fragment were available, primers specific for the ends were designed and were named OT ACS 38 P1 (SEQ ID NO: 18) and OT ACS 38 P2 (SEQ ID NO: 19). The fragment was amplified in its entirety using a high fidelity polymerase. The PCR reaction was carried out on 100 ng of genomic DNA of *Penicillium* sp. CBS 109899, with 1 unit of PLATINUM Pfx DNA polymerase (Life Technologies, Inc.) and using an MJ Research thermal cycler model PTC-200. The amplification product was analyzed on 0.8% agarose gel. A 3.8 kb fragment was directly subcloned into the vector pCR4-TOPO (Invitrogen), sequenced (SEQ ID NO: 1) and named OT ACS 38.1.

8.3. Analysis of the Sequence of the cDNA and of the Gene

An amino acid sequence was deduced from the cDNA and analyzed (SEQ ID NO: 3). All the internal peptide sequences of the phytase obtained by microsequencing were found within this amino acid sequence, confirming that the cDNA sequenced corresponds to the phytase of interest. In addition, the deduced amino acid sequence contains the specific sites for binding (RHGXRXP) (SEQ ID NO: 24) and nucleophilic attack (HD) of phosphates, which characterize the phytases belonging to the group of histidine acid phosphatases. Alignment of the cDNA sequence with that of the genomic DNA fragment OT ACS 38.1 made it possible to determine the precise limits of the gene of interest and to locate the introns that it contains.

EXAMPLE 9

Homologous Sequence Search 9.1. Construction of a Cosmid Library of the *Penicillium Funiculosum* IMI 134756 Strain

*P. funiculosum* IMI 134756 was cultured in liquid MN-Uri medium (28° C., 180 rpm, 2 days). The mycelium was recovered by filtration, and ground in liquid nitrogen. Extraction of the genomic DNA was carried out in 5 ml of lysis buffer (1% SDS, 2% Triton X-100, 100 mM NaCl, 1 mM EDTA, 10 mM Tris, pH 8.0) and 5 ml of phenol on 1 g of ground material. After purification of the aqueous phase with phenol/chloroform and chloroform, the genomic DNA was precipitated by adding 2 volumes of ethanol.

The product of partial digestion of 20 pg of genomic DNA with the SalI restriction enzyme was loaded onto an agarose (low melting point) gel in order to be subjected therein to pulsed field electrophoresis (18 hours, 5 V/cm) in a 0.5×TBE buffer. After staining with ethidium bromide, the DNA fragments 30 to 40 kb in length were released from the gel by digestion with β-agarase (GIBCO-BRL) and precipitated with ethanol. An aliquot of this genomic DNA was ligated into the vector pMOCosX [Orbach (1994), GENE 150, pp 159-162] digested with XhoI and dephosphorylated with calf intestine phosphatase beforehand. The ligation product, brought into contact with the elements of the λ phage (Packaging Protocol—STRATAGENE; Gigapack Gold-11), made it possible to transfect an *E. coli* strain Q358 (Maniatis et al., 1982). After plating out on Luria and Bertani (LB) agar medium supplemented with 50 pg/ml of ampicillin, the colonies were taken up in 50 96-well microtitration plates and cultured overnight in 150 µl of LB supplemented with 50 pg/ml of ampicillin. The cultures were replicated on Hybond N+ membranes (AMERSHAM) before being supplemented with glycerol at a final concentration of 50% and stored at −80° C.

9.2. Screening the Cosmid Library with the Probe OT ACS 29.1

Analysis by Southern blotting on the genomic DNA of the *P. funiculosum* IMI 134756 strain was carried out with the probe OT ACS 29.1. The membrane onto which the genomic DNA, digested with several restriction endonucleases and separated by electrophoresis beforehand, is transferred was prehybridized in the hybridization buffer (7% SDS; 0.5M sodium phosphate, pH 7.0) for 10 minutes at 65° C. The probe was labeled with α-$^{32}$P dCTP using the DNA labeling kit (Amersham). The labeled probe was added to the hybridization buffer and the mixture was heated for 5 min at 100° C. before use. The hybridization was carried out for 6 h at 65° C. After hybridization, the membrane was rinsed 3 times for 15 min at 65° C. in a rinsing buffer (1% SDS; 0.1M sodium phosphate, pH 7.0), and then exposed. This analysis revealed only one signal. The genome of P. funiculosum IMI 134756 therefore contains only one copy of the gene of interest. The cosmid library was then screened under the same stringent conditions using the probe OT ACS 29.1, which revealed several signals on membranes no. 15, 19 and 48. The cosmid 15F10, relating to membrane no. 15, was thus identified as containing a DNA sequence which hybridized with the probe OT ACS 29.1. Restriction analysis was carried out on the DNA of this cosmid in order to determine the position of the corresponding gene. The gene was named phyF. Cloning and sequencing of a 1.3 kb NcoI fragment of the cosmid 15F10 showed strong homology with the sequence OT ACS 29.1. The complete phyF gene was located on a 2.7 kb EcoRV—EcoRI fragment, which was cloned and sequenced (SEQ ID NO: 4).

Analysis of the sequence (SEQ ID NO:4) shows a 790 bp promoter region and a beginning of the sequence encoding phyF at ATG 791. The phyF gene has 1737 bp (position 791-2527).

EXAMPLE 10

Recombinant Expression of the Gene Contained in OT ACS 38.1 (SEQ ID NO: 1)

10.1. Introduction of Multiple Copies of the Gene into P. funiculosum IMI. 134756

In order to validate the cloned gene (OT ACS 38.1), it was undertaken to introduce multiple copies into the genome of the P. funiculosum IMI 134756 strain, which produces little phytase, and to observe whether the transformed clones exhibited an increase in productivity.

For this, P. funiculosum IMI 134756 was cotransformed according to the technique described in patent WO 00/68401, with the plasmid containing the fragment OT ACS 38.1 and the plasmid pAN7-1 (Punt et al., 1987; Gene, 56:117-24) which allows selection with hygromycin. After transformation, the integration of multiple copies of the gene of interest was verified by Southern analysis using the molecular probe OT ACS 29.1. The Southern analysis was carried out according to the conditions described in example 9, on the genomic DNA of the candidates digested with the EcoRI restriction endonuclease.

The positive candidates were cultured under conditions of induction for the phytase in 50 ml of a medium composed of 20 g/[lacuna] calcium phytate, 10 g/l glucose, 8 g/l NH$_4$NO$_3$, 5 g/l KCl and 5 g/l MgSO$_4$.7H$_2$O, and supplemented with 1 ml/l of a solution of trace elements (2.2% ZnSO$_4$.7H$_2$O, 1.1% H$_3$BO$_3$, 0.5% MnCl$_2$.4H$_2$O, 0.5% FeSO$_4$.7H$_2$O, 0.17% CoCl$_2$.6H$_2$O, 0.16% CuSO$_4$.5H$_2$O, 0.15% Na$_2$MoO$_4$.2H$_2$O and 5.0% Na$_2$ EDTA, pH at 6.5). The phytase activity in the medium was measured over time.

The results obtained for the analysis of 2 candidates, with nontransformed P. funiculosum IMI 134756 used as controls, are given in table 2.

Table 2: Monitoring the Phytase Activity (in U/ml) in the Cultures of 2 Candidates Consisting of P. Funiculosum IMI 134756 Transformed with the Fragment OT ACS 38.1, and of Wild-Type P. Funiculosum IMI 134756

| | Days | | | | | | | | | | |
|---|---|---|---|---|---|---|---|---|---|---|---|
| | D1 | D2 | D3 | D4 | D5 | D6 | D7 | D8 | D11 | D12 | D14 |
| IMI 134756 | 0 | 0 | 0 | 1.1 | 0.8 | 0.9 | 1.3 | 1.2 | 0.9 | 1.5 | 1.4 |
| Candidate 1 | 0 | 0 | 0 | 2 | 1.3 | 1.2 | 2.2 | 1.7 | 2.5 | 3.6 | 4.1 |
| Candidate 2 | 0 | 0 | 0 | 2.2 | 1.8 | 1.4 | 1.4 | 1.3 | 2 | 2.6 | 3 |

The monitoring of phytase activity in the medium shows that, for the two candidates tested which have integrated multiple copies of OT ACS 38.1 into their genome, the phytase productivity was multiplied 2- to 2.5-fold. This result tends to confirm that the gene of interest, contained in the fragment OT ACS 38.1, encodes a phytase and that the phytase productivity of a Penicillium strain can be increased by multiplying the number of copies of the gene within its genome.

10.2: Expression of the Gene Under the Control of a Heterologous Promoter

The expression cassette containing the promoter and the terminator of the csl31 gene described in patent WO 00/68401 was used to express the region of the genomic DNA fragment OT ACS 38.1 encoding the phytase of interest. For this, after an SwaI site had been introduced at the end of the promoter, the expression cassette was digested with the SwaI/SpeI restriction endonucleases. The region encoding the phytase contained in the genomic DNA fragment OT ACS 38.1 was amplified using the following primers:

phyGoamp4 5'TAGATATCACGATGCTCAAGCTATATG-TAGCTGC 3' (SEQ ID NO: 22) and phyGoamp5 5'ATACTAGTTTAGGACGTAGCATTCT-TCGGAATAG 3' (SEQ ID NO: 23).

The PCR reaction was carried out using an MJ Research thermal cycler model PTC-200 with 10 μmol of each primer and 1 unit of PLATINUM Pfx DNA polymerase (Life Technologies, Inc.) in 50 μl of buffer relating to this polymerase (Life Technologies, Inc.). The PCR product was digested with the EcoRV and SpeI restriction endonucleases and ligated into the vector pBCMT. The plasmid thus obtained was named pCP.

P. funiculosum IMI 134756 was cotransformed according to the technique described in patent WO 00/68401, with the plasmid containing the fragment OT ACS 38.1 and the plasmid pAN7-1 (Punt et al., 1987; Gene, 56:117-24), which makes it possible to select with hygromycin. The integration of the pCP cassette into the genome of the candidates was verified by Southern analysis using the molecular probe OT ACS 29.1, on the genomic DNA of 8 candidates digested with the EcoRI restriction endonuclease. After analysis, 4 cotransformants were selected and cultured under conditions of induction for the csl31 promoter. The expression of the gene was analyzed and the phytase activity was measured.

The 4 candidates selected were cultured in 125 ml Erlenmeyer flasks in 50 ml of minimum medium supplemented with 1% of Corn Steep Liquor. The mycelium was collected after culturing for 48 h and 72 h at 28° C., 180 rpm, and Northern analysis was carried out for each sample, with the probe OT ACS 29.1, on 20 μg of total RNA (Sambrook et al., 1989, Molecular Cloning: A Laboratory Manual). After the membrane had been rinsed, the signals were visualized using a STORM phosphoimager (Molecular Dynamics).

The results show a signal exclusively in the candidates transformed with pCP, and a lack of signal in the nontransformed control, demonstrating that the gene is expressed under the control of the csl31 promoter.

In parallel, the phytase activity was measured in the supernatants of each of the cultures. The results are given in table 3.

Table 3: Measurement of the Phytase Activity (in U/ml) in the Culture Supernatants of the 4 Candidates Transformed with pCP and Cultured Under Conditions of Induction for the csl31 Promoter for 48 h and 72 h. *P. Funiculosum* IMI 134756 was Used as a Control.

|  | 48 h | 72 h |
|---|---|---|
| Control | 0 | 0 |
| Candidate 1 | 1 | 1.2 |
| Candidate 2 | 0.8 | 1.7 |
| Candidate 3 | 0.7 | 1.2 |
| Candidate 4 | 1.7 | 2.9 |

Analysis of the results shows that the phytase activity is present only in the supernatants corresponding to the candidates transformed with pCP. This result is in agreement with the expression of the gene and demonstrates that the genomic DNA fragment contains a gene encoding a phytase.

EXAMPLE 11

Optimization of the Conditions for Culturing the *Penicillium* sp. CBS 109899 Strain 11.1. Influence of Agitation on the Phytase Production The fermentations were carried out under the conditions of example 3, the rate of agitation ranging from 400 to 450 rpm (Table 4).

Table 4: Activities Obtained at the End of Fermentation as a Function of Agitation

| Fermenter volume | Agitation rpm | Activity U/mL |
|---|---|---|
| 30 L | 400 | 66 |
| 30 L | 425 | 48 |
| 30 L | 450 | 36 |

These results show that the increase in agitation had a negative effect on the phytase production by the native *Penicillium* sp. CBS 109899 strain.

11.2. Influence of the Source of Nitrogen on the Phytase Production

The fermentations were carried out under the conditions of example 3. The only parameter which varies is the source of nitrogen (rice bran), which is substituted with a different source of nitrogen, soya bran (Table 5).

Table 5: Activities Obtained at the End of Fermentation as a Function of the Source of Nitrogen

| Source of nitrogen | Activity (%) |
|---|---|
| Rice bran | 100% |
| Soya bran | 128% |

These results show that the source of nitrogen has an effect on the phytase production by the native *Penicillium* sp. CBS 109899 strain; in particular, the soya bran as source of nitrogen promotes phytase production.

11.3. Influence of the Source of Phytate on the Phytase Production

The fermentations were carried out under the conditions of example 3. The only parameter which varies is the $Ca^{++}$ phytate, which is substituted with the $Ca^{++}$ and $Mg^{++}$ double salt (Table 6).

Table 6: Activities Obtained at the End of Fermentation as a Function of the Source of Phytate

| Phytate salts | Activity (%) |
|---|---|
| $Ca^{++}$ salts | 100% |
| $Ca^{++}$ and $Mg^{++}$ salts | 120% |

These results show that the source of phytate has an effect on the phytase production by the native *Penicillium* sp. CBS 109899 strain; in particular, the calcium and magnesium double salt as a source of phytate makes it possible to improve phytase production compared to the calcium salt.

11.4. Influence of the Amount of Phytate on the Phytase Production

The fermentations were carried out under the conditions of example 3. The only parameter which varies is the amount of phytate present in the fermentation medium (Table 7).

Table 7: Activities Obtained at the End of Fermentation as a Function of the Amount of Phytate

| $Ca^{++}$ phytate in g/L | Activity (%) |
|---|---|
| 20 | 100% |
| 15 | 70% |
| 10 | 60% |
| 0 | 1% |

These results show that the phytase production by the native *Penicillium* sp. CBS 109899 strain significantly increases with the amount of phytate present in the fermentation medium.

EXAMPLE 12

Zootechnical Efficacy of the Phytase Produced by the *Penicillium* sp. CBS 109899 Strain 12.1. Effect of a Phytase-Supplemented Diet on Phosphorus Digestibility by Roosters The experiment was carried out on 20 roosters. The animals were divided into two groups of 10, one group of treated animals and one group of control animals, and then reared individually in cages. They were then fed with a feedstuff based on maize and soybean deficient in digestible phosphorus (P), supplemented with 702 IU (International Unit=amount of phytase capable of releasing 1 µmol of phosphate per minute at 37° C., pH 5.5, solution of sodium phytate at 10 g/l) of phytase per kg of feedstuff for the group of treated animals.

The feces of the animals were collected at two and three days after the start of the experiment in order to analyze phosphorus excretion. The phosphorus digestibility corresponds to the percentage of phosphorus assimilated by the animals compared to the amount ingested. This percentage is deduced from the excreted amount found in the feces (Table 8).

Table 8: Phosphorus Ingestion, Excretion and Digestibility

|  | Phosphorus | | |
| --- | --- | --- | --- |
|  | Ingestion (g/kg) | Excretion (g/kg) | Digestibility (%) |
| Basic feedstuff | 0.804 ± 0.003 | 0.319 ± 0.019 | 60.3 ± 2.5 |
| Feedstuff supplemented with 702 IU/kg | 0.801 ± 0.011 | 0.255 ± 0.028 | 68.1 ± 4.4 |

The results in table 8 clearly show that supplementing a basic feedstuff deficient in digestible phosphorus with the phytase according to the invention significantly reduces ($p<0.05$) phosphorus excretion. This effect reflects an increase in phosphorus digestibility in the animals fed with the supplemented feedstuff. It shows the efficacy of the phytase according to the invention in releasing the nondigestible phosphorus of the feed intake.

12.2. Effect of a Phytase-Supplemented Diet on the Growth of Chickens

The experiment was carried out on 210 chickens of the Ross 308 race. The animals were divided into six groups of 35, four groups of animals treated with various doses of phytase, one group of untreated negative control animals, and one group of positive control animals treated with inorganic phosphorus. The animals are reared in a proportion of five animals per cage, and fed for 13 days (from 9 days old to 22 days old). The basic feedstuff, consisting of maize and soybean, and deficient in digestible phosphorus (P), is supplemented with 4 different concentrations of phytase: 243, 433, 738 and 1234 IU of phytase per kg of feedstuff for the four groups of treated animals, and with 0.1% of inorganic phosphorus in the form of monocalcium or bicalcium phosphate for the positive controls.

Growth was estimated by measuring the body weights of the animals at the beginning and at the end of the experiment. These measurements make it possible to determine the gain in body weight and the consumption index (CI). The consumption index corresponds to the amount of feedstuff consumed relative to the gain in body weight. For a given amount of feedstuff, a decrease in the index signifies an increase in the weight gained by the animal, i.e. a better assimilation of the feedstuff by the animal. The results are given in table 9.

Table 9: Effect of the Phytase on the Growth of Chickens

| Treatment | Negative controls | 243 IU/kg | 433 IU/kg | 738 IU/kg | 1234 IU/kg | Positive controls |
| --- | --- | --- | --- | --- | --- | --- |
| Weight gain (g) | 216 ± 76 | 369 ± 88 | 435 ± 82 | 452 ± 97 | 497 ± 81 | 461 ± 72 |
| CI | 2.28 ± 0.91 | 1.74 ± 0.52 | 1.57 ± 0.34 | 1.61 ± 0.44 | 1.51 ± 0.26 | 1.51 ± 0.23 |

The results show that supplementing a basic feedstuff deficient in digestible phosphorus with 243, 433, 738 and 1234 IU/kg of phytase according to the invention results in a weight gain which is increased, respectively, 1.7-, 2.0-, 2.1- and 2.3-fold. The highest doses even make it possible to obtain weight gains which are greater than supplementing the feedstuff with inorganic phosphorus. This supplementation also makes it possible to increase the consumption index by on average 33%.

12.3. Effect of a Phytase-Supplemented Diet on Bone Mineralization in Chickens

The experiment was carried out on 210 chickens of the Ross 308 race. The animals were divided into six groups of 35, four groups of animals treated with various doses of phytase, one group of untreated negative control animals, and one group of positive control animals treated with inorganic phosphorus. The animals are reared in a proportion of five animals per cage, and fed for 13 days (from 9 days old to 22 days old). The basic feedstuff, consisting of maize and soybean, and deficient in digestive phosphorus (P), is supplemented with 4 different concentrations of phytase: 243, 433, 738 and 1234 IU of phytase per kg of feedstuff for the four groups of treated animals, and with 0.1% of inorganic phosphorus in the form of monocalcium or bicalcium phosphate for the positive controls.

At day 14, a tibia is removed from each animal. Each tibia is weighed and incinerated, and its ash, calcium and phosphorus contents are analyzed. The results are given in table 10.

Table 10: Effect of the Phytase on Bone Mineralization in Chickens

| Treatment | Negative controls | 243 IU/kg | 433 IU/kg | 738 IU/kg | 1234 IU/kg | Positive controls |
| --- | --- | --- | --- | --- | --- | --- |
| Tibial phosphorus (mg) | 89.1 | 138.2 | 157.8 | 180.1 | 215.9 | 184.1 |
| SD | ±22.5 | ±21.4 | ±28.1 | ±41.2 | ±37.6 | ±14.8 |
| Tibial calcium (mg) | 43 | 66.7 | 76.8 | 87.8 | 103.6 | 89.7 |
| SD | ±9.6 | ±9.3 | ±13.6 | ±18.6 | ±19.3 | ±8.0 |
| Tibial ash (mg) | 309 | 473 | 527 | 594 | 683 | 602 |
| SD | ±71 | ±54 | ±71 | ±102 | ±106 | ±42 |

These results clearly show, for all the concentrations tested, a positive effect of supplementing the feedstuff with a phytase according to the invention, on bone mineralization in chickens. In particular, the phytase according to the invention promotes calcium and phosphorus mineralization of the bones, and also their ash mass. In addition, for each of the parameters measured, a dose effect is observed.

12.4. Effect of a Phytase-Supplemented Diet on Phosphorus and Calcium Digestibility in Pigs The experiment was carried out on 7 pigs with an average approximate weight of 70 kg. An ileorectal anastomosis was performed by surgery on the animals in order to be able to quantitatively collect their ileal content. They were reared individually for the needs of the experiment.

The animals were fed with three feedstuffs based on maize and soybean. Supplementation was provided at 300 and 600

IU per kg of feedstuff. Each animal was adapted to a feedstuff for 6 consecutive days. The ileal content was collected on day 7, and then the animal's feedstuff was changed. The amount of calcium and of phosphorus in the ileal content was analyzed, and then the digestibility of these two elements was measured. The results are given in table 11.

Table 11: Effect of the Phytase on Calcium and Phosphorus Digestibility in Pigs

|  | Control | 300 IU/kg | 600 IU/kg |
|---|---|---|---|
| Ca digestibility (%) | 42.73 ± 7.40 | 45.26 ± 2.49 | 47.09 ± 8.14 |
| P digestibility (%) | 39.46 ± 11.86 | 43.06 ± 9.11 | 47.52 ± 15.23 |

Supplementing the feedstuff with a phytase according to the invention significantly increases the calcium and phosphorus digestibility. The calcium digestibility is increased by 5.6 and 9.3%, respectively, for the feedstuffs supplemented with 300 and 600 IU per kg of feedstuff, and the phosphorus digestibility is increased by 8.4 and 17%, respectively, for the feedstuffs supplemented with 300 and 600 IU per kg of feedstuff.

12.5. Effect of a Phytase-Supplemented Diet on Phosphorus Digestibility on Piglets The experiment was carried out on 12 piglets with an average approximate weight of 11 kg. The animals were divided into two groups of 6, one group of treated animals and one group of control animals, and then reared individually in cages. They were then fed for 26 days with a feedstuff based on maize and soybean, deficient in digestible phosphorus (P), supplemented with 481 IU of phytase per kg of feedstuff.

The feces of the animals were collected for 5 days, from day 21 of the experiment, in order to analyze their phosphorus and calcium content. The phosphorus digestibility corresponds to the percentage of phosphorus and calcium assimilated by the animals compared to the amount ingested. This percentage is deduced from the excreted amount found in the feces (table 12).

Table 12: Effect of the Phytase on Phosphorus Digestibility in Piglets

|  | Ingestion (g) | Excretion (g) | Digestibility (%) |
|---|---|---|---|
| Phosphorus |  |  |  |
| Controls | 1.007 ± 0.127 | 0.800 ± 0.078 | 20.11 ± 5.79 |
| 481 IU/kg | 1.145 ± 0.124 | 0.573 ± 0.111 | 50.28 ± 6.52 |
| Calcium |  |  |  |
| Controls | 1.873 ± 0.237 | 1.228 ± 0.180 | 34.2 ± 7.73 |
| 481 IU/kg | 2.131 ± 0.234 | 1.102 ± 0.102 | 48.62 ± 8.44 |

These results show that supplementing the feedstuff with a phytase according to the invention increases the phosphorus digestibility by 250% and the calcium digestibility by 42%.

12.6. Effect of a Phytase-Supplemented Diet on the Growth of Piglets

The experiment was carried out on 12 piglets with an average approximate weight of 11 kg. The animals were divided into two groups of 6, one group of treated animals and one group of control animals, and then reared individually in cages. They were then fed for 26 days with a feedstuff based on maize and soybean, deficient in digestible phosphorus (P), supplemented with 481 IU of phytase per kg of feedstuff.

Growth was estimated by measuring the bodyweights of the animals at the beginning and at the end of the experiment. These measurements made it possible to determine the gain in bodyweight and the consumption index (CI). The results are shown in table 13.

Table 13: Effect of the Phytase on the Growth of Piglets

| Treatment | Controls | 481 IU/kg |
|---|---|---|
| Initial bodyweight (kg) | 6.81 ± 0.69 | 6.75 ± 0.88 |
| Final bodyweight (kg) | 13.34 ± 1.58 | 14.86 ± 1.41 |
| Gain in bodyweight (kg) | 6.53 ± 1.72 | 8.11 ± 1.66 |
| CI | 2.31 ± 1.85 | 1.63 ± 0.88 |

The results show that supplementing a basic feedstuff deficient in digestible phosphorus with 481 IU/kg of phytase according to the invention results in a 24% increase in weight gain. This supplementation also significantly decreases the consumption index.

12.7. Effect of a Phytase-Supplemented Diet on Bone Mineralization in Piglets

The experiment was carried out on 12 piglets with an average approximate weight of 11 kg. The animals were divided into two groups of 6, one group of treated animals and one group of control animals, and then reared individually in cages. They were then fed for 26 days with a feedstuff based on maize and soybean, deficient in digestible phosphorus (P), supplemented with 481 IU of phytase per kg of feedstuff.

On day 27 of the experiment, a tibia is removed from each animal. Each tibia is weighed and incinerated, and its mineral, calcium and phosphorus content is analyzed. The results are given in table 14.

Table 14: Effect of the Phytase on Bone Mineralization in Piglets

| Treatment | Controls | 481 IU/kg |
|---|---|---|
| Tibial phosphorus (%) | 1.66 ± 0.10 | 2.18 ± 0.09 |
| Tibial calcium (%) | 3.56 ± 0.30 | 4.69 ± 0.42 |
| Minerals (%) | 10.45 ± 0.69 | 13.12 ± 0.55 |

The results show that supplementing a basic feedstuff deficient in digestible phosphorus with 481 IU/kg of phytase according to the invention results in a significant increase in bone mineralization in piglets. In particular, the phytase according to the invention favors calcium and phosphorus mineralization of the bones, and also their mineral mass.

The invention claimed is:

1. An isolated polynucleotide comprising a nucleotide sequence encoding only a phytase, or its full length complementary sequence, wherein the polynucleotide is selected from the group consisting of:
   (a) a polynucleotide having a sequence comprising nucleotide residues 1381-1490, 1551-1702, and 1765-3118 of SEQ ID NO:1;
   (b) a polynucleotide having a sequence comprising nucleotide residues 89-1711 of SEQ ID NO:2;
   (c) a polynucleotide having a sequence comprising nucleotide residues 1381-3118 of SEQ ID NO: 1;
   (d) a polynucleotide having a sequence comprising SEQ ID NO:1;
   (e) a polynucleotide having a sequence comprising SEQ ID NO:2;
   (f) a polynucleotide having a sequence encoding the amino acid sequence of SEQ ID NO:3;
   (g) a polynucleotide having a sequence at least 95% homologous to the sequence of the polynucleotide of (a), (b), (c), (d), (e),
   (h) a polynucleotide having a sequence complementary to the full length sequence of the polynucleotide of (a), (b), (c), (d), (e), (f), or (g); and
   (i) a polynucleotide having a sequence comprising at least 100 contiguous nucleotides of the sequence of the polynucleotide of (a), (b), (c), (d), (e), (f), (g), or (h), wherein the at least 100 contiguous nucleotides encode an active fragment of the phytase.

2. The isolated polynucleotide of claim 1, wherein the polynucleotide is (d) or (e).

3. The isolated polynucleotide of claim 1, wherein the polynucleotide is (f).

4. The isolated polynucleotide of claim 1, wherein the polynucleotide is obtained from a fungus of the *Penicillium* genus.

5. The isolated polynucleotide of claim 4, wherein the fungus is *Penicillium* sp. Deposit No. CBS 109899.

6. A chimeric gene comprising:
   (a) a promoter, which is functional in a host organism;
   (b) a polynucleotide of claim 1; and
   (c) a terminator element, which is functional in the host organism; wherein the promoter, polynucleotide, and terminator element are functionally linked.

7. The chimeric gene of claim 6, further comprising a nucleotide sequence encoding a signal peptide or a transit peptide, which is functional in the host organism.

8. A vector, comprising the chimeric gene of claim 6.

9. The vector of claim 8, wherein the vector is a plasmid, phage, or virus.

10. An isolated transformed host cell, comprising the chimeric gene of claim 6.

11. The host cell of claim 10, wherein the host cell is a microorganism.

12. The host cell of claim 11, wherein the transformant is a microorganism selected from the group consisting of bacteria, fungi, yeasts, and viruses.

13. The host cell of claim 12, wherein the microorganism is a bacterium selected from the genera consisting of *Corynebacterium, Bacillus, Streptomyces,* and *Escherichia*.

14. The host organism of claim 13, wherein the microorganism is the bacterium *Escherichia coli*.

15. The host cell of claim 12, wherein the microorganism is a fungus selected from the genera consisting of *Penicillium, Aspergillus, Chrysosporium,* and *Trichoderma*.

16. The host cell of claim 12, wherein the microorganism is a yeast selected from the genera consisting of *Saccharomyces, Kluyveromyces,* and *Pichia*.

17. A method for producing an extract having phytase activity, comprising:
   (a) culturing at least one organism having a nucleotide sequence comprising a polynucleotide of claim 1, under conditions which allow phytase expression;
   (b) removing the organism from the culture medium;
   (c) rupturing the cells of the organism;
   (d) centrifuging the ruptured cells; and
   (e) recovering the resulting supernatant, wherein the supernatant has phytase activity.

18. The method for producing an extract having phytase activity of claim 17, wherein the organism is a microorganism.

19. The method for producing an extract having phytase activity of claim 18, wherein the microorganism is a fungus.

20. The method for producing an extract having phytase activity of claim 19, wherein the fungus is a fungus of the *Penicillium* genus.

21. The method for producing an extract having phytase activity of claim 20, wherein the fungus is *Penicillium* sp. Deposit No. CBS 109899.

22. A method for producing an extract having phytase activity, comprising:
   (a) culturing at least one organism having a nucleotide sequence comprising a polynucleotide of claim 1, under conditions which allow phytase expression; and
   (b) removing the organism from the culture medium, wherein the culture medium has phytase activity.

23. The method for producing an extract having phytase activity of claim 22, wherein the organism is a microorganism.

24. The method for producing an extract having phytase activity of claim 23, wherein the microorganism is a fungus.

25. The method for producing an extract having phytase activity of claim 24, wherein the fungus is a fungus of the *Penicillium* genus.

26. The method for producing an extract having phytase activity of claim 25, wherein the fungus is *Penicillium* sp. Deposit No. CBS 109899.

27. A method for producing a phytase, comprising:
   (a) culturing at least one organism having a nucleotide sequence comprising a polynucleotide of claim 1, under conditions which allow phytase expression;
   (b) removing the organism from the culture medium;
   (c) rupturing the cells of the organism;
   (d) centrifuging the ruptured cells;

(e) recovering the resulting supernatant, wherein the supernatant has phytase activity;
(f) obtaining phytase from the supernatant; and
(g) purifying the phytase.

28. The method for producing a phytase of claim 27, wherein the organism is a microorganism.

29. The method for producing a phytase of claim 28, wherein the microorganism is a fungus.

30. The method for producing a phytase of claim 29, wherein the fungus is a fungus of the *Penicillium* genus.

31. The method for producing a phytase of claim 30, wherein the fungus is *Penicillium* sp. Deposit No. CBS 109899.

32. A method for producing a phytase, comprising:
    (a) culturing at least one organism having a nucleotide sequence comprising a polynucleotide of claim 1, under conditions which allow phytase expression;
    (b) removing the organism from the culture medium;
    (c) obtaining phytase produced in the culture medium; and
    (d) purifying the phytase.

33. The method for producing a phytase of claim 32, wherein the organism is a microorganism.

34. The method for producing a phytase of claim 33, wherein the microorganism is a fungus.

35. The method for producing a phytase of claim 34, wherein the fungus is a fungus of the *Penicillium* genus.

36. The method for producing a phytase of claim 35, wherein the fungus is *Penicillium* sp. Deposit No. CBS 109899.

37. A method for producing an extract having phytase activity, comprising:
    (a) culturing at least one host cell of claim 10;
    (b) removing the host cell from the culture medium;
    (c) rupturing the cells;
    (d) centrifuging the ruptured cells; and
    (e) recovering the resulting supernatant, wherein the supernatant has phytase activity.

38. A method for producing an extract having phytase activity, comprising:
    (a) culturing at least one host cell of claim 10; and
    (b) removing the host cell from the culture medium, wherein the culture medium has phytase activity.

39. A method for producing a phytase, comprising:
    (a) culturing at least one host cell of claim 10;
    (b) removing the host cell from the culture medium;
    (c) rupturing the cells of the host cell;
    (d) centrifuging the ruptured cells;
    (e) recovering the resulting supernatant, wherein the supernatant has phytase activity;
    (f) obtaining phytase from the supernatant; and
    (g) purifying the phytase.

40. A method for producing a phytase, comprising:
    (a) culturing at least one host cell of claim 10;
    (b) removing the host cell from the culture medium;
    (c) obtaining phytase produced in the culture medium; and
    (d) purifying the phytase.

* * * * *

SEQUENCE LISTING

<160> NUMBER OF SEQ ID NOS: 24

<210> SEQ ID NO 1
<211> LENGTH: 3753
<212> TYPE: DNA
<213> ORGANISM: Penicillium sp. CBS 109899
<220> FEATURE:
<221> NAME/KEY: Intron
<222> LOCATION: (1491)..(1550)
<220> FEATURE:
<221> NAME/KEY: Intron
<222> LOCATION: (1703)..(1764)

<400> SEQUENCE: 1

```
ggctttgctg gtgcggggtg agtccgctgg ttggctcgct tctgctgttg cgatttcagc      60
gtcggcttgg gctatgatag ccgccagggt ggctgcgact cggtcatgga gctgtgcgag     120
agtctcacca cgtcgcggtg ggatcacaaa tggtttgtag agactttcag ggttttcggc     180
aaggcaagtt gagaaatgag ggtacagaac atttgccgaa acgggagcgg gaggttcaaa     240
tgtgatgcct ccgaaccatt cgctatgtta agctgtcaa tcttctttt cttaatcata       300
ccaatggatg actgccctac cctaatccat tttcgactct gacgttgaga tctgtcccag     360
cgtcaagatt tatctcggct gactgggatt tcttcgctaa ctgctccacg gttggctgga     420
ttgtctgcat gcatcgatag aacggactag aataaatccg aaatggtttt gggatgaagt     480
tagggctact aatatgcgat gcgagctcat gggattgttt gacaccgctt ggattcaagg     540
ttgggtctgc gccattgccg gttggtgtag gaaattctgg aatgtattct tgtttgtcga     600
aatcgatttc ccagttgtta cgattctagc caagaagatt aatacatcca gttctcaaat     660
aaagctcaag ggacatgctt actccatggc gaacgagata gattgtgtct agaggcatcg     720
cgtcgaaagg ccgtcttggg actcttggct gtattgatag atttgattga acagttgtaa     780
gttctcaatt tctctagcct ttatacttct agaggcaaac tctccatcaa agagtttgct     840
tcaataccta cacctggaat ccactttccg atagactgca atgcccacta taactagtgc     900
ccaactgtgg tccctaagtt ccatctaact tcttgagatc tctcttggac aaacttaaac     960
caaagcgagc cgacataatt gcctcatctg gctgatcaga taagaataa atcaacaga      1020
ggataacgaa ttaaagcgcc ttgtttcaat caatttcag taccgacca tgcaccttct     1080
tggaccagtt attgtcggca aatgtaaatg cttgggatag gcccaatgaa ctcactatga    1140
ggccccaaat catttctagc taccccagat tttcaaaagc cggggtagaa atatggtgct    1200
tgctatgttg tctattcggg caggaggtcg tgtgacagag agagttataa ataaccttgg    1260
aaccttggaa atcttcgtaa tgtatacttt gtaccggact ttcaaggttt catttaacat    1320
tcattgtcct ttggttcata ttctatacag aagaatcaga actgtatttc gattaccacg    1380
atgctcaagc tatatgtagc tgcctgtctg gtggtggccg tgtttctat cccgacagac     1440
cctaccgtaa cccaagtccc ggattacttc caaacgagct atgggccata tgcaggtatg    1500
gaaatatgcg taccttgtca aaggctatta gggctcaaca ggctacaggt gctaccaaag    1560
ccggaggcgc tccgttcctt gcgcaaacca atccgatcta ttcccagccg acctacgtcg    1620
caaacacgcc attggtgaca actcttccca tatctggtga accccatgac ggaaacatat    1680
tcggctggat ggggactttg aggtatgtat tatctttcgc tgaagtaccg ttagtacgga    1740
tgaaactgat cttagacaaa acagtccta ccaacccagc cctgatggat ttggcgtgga    1800
tgaatatcct ctccctcccg gtgcaaacat tacgcaaatc catatggtgc atcgccatgg    1860
```

```
ctcgcgctat ccgacgtcaa attccgcaat cagcgattgg gctaagaaaa taatgcagta       1920
tcgatccaac ggcacagtgt tctcaggcga acttgagttt ctgaacgctt ggaactatca       1980
gctcggacag gcagagctaa cagcacgagg tcggcaagag ttattcgaca gcgggattct       2040
acattggttc aattatggaa agctctacga tcctgcatca aaaatcatag ctcgcacaac       2100
aacgatggtg aggatgttgc aatcagcgga gaacttcctc aatggatttt ttggtccaaa       2160
ctggactaat aatgcgacgc ttgaagtcat tattgaaagt accgggttca acaactccct       2220
cgcagggaat gatatgtgtc gcaatgcaaa aaatacatcg gggggcgacg cagtaaatga       2280
atggaccgcg ctatacttgc agaaagcgac aaatcgcttc agaagtgaaa tatctggaag       2340
tctgaactgg actgttgacg acacgtacaa tgcacagtcg atgtgcccat acgagactgt       2400
tgcacttggt tatagtccgt tttgtacatt gttttcttgg gaggaatggc aagggttcca       2460
gtatgttaac gacttgaacc tctatgggaa ctatggcatg ggttctccag ttggccgcgc       2520
cattggactt ggatttgtcg aagaattgat tgcacggctg caggggcaaa tcccaaaccc       2580
ccctgaagac tcaattgggt tcaatcaatc gctagatgat agtgccgcga ctttccctct       2640
caaccaaaca atctacttcg actttagcca cgacaacgag atgttctcga tgttgactgc       2700
cctgggcttg acacagtttg gggactacct ctctcccacg aagccctctg cggatcgttc       2760
gttgattgga agccatatcg tcccgttctc ggctaccttt gtatttgaga tcatcaaagc       2820
acctggtctt gtacgagaga atcgatcaaa gtattgcggt gaaagtgtgt atgaaaatac       2880
gagcgaagaa acaacctaca tacatctcgt cattaaccag aggactgttc ctcttggtca       2940
aagcatttca gcatgcgggc aacgagatga tggttggtgt gaaatttccg ccttcattca       3000
ggcgcagaaa gaaaacatcg tgaaggcaaa ttacgaggaa agctgtttcg gaaattggag       3060
catcccggcg tacggcgaga tcagggatgg cgctattccg aagaatgcta cgtcctaact       3120
gctatattag acgccctcga aagtttagat tggagatact cggacaaact cgcttcattc       3180
aatagctaga agggcaacta tgttcgtttc acttacttcg ataccagata cacgtagtat       3240
gatgcaagta ttccgagttc tcacatgaat attcgggcta agtctgctga agacatcct        3300 gattaaatct agttgtcagt tgccggtgcc accgataact gacagctaca gcgagtatat       3360
tggtgttatg tatataatta actaactact gttaaggcgt gtgagtaatc gatacataaa       3420
tctctcatag gtcaaccgtg gcaagagtta tcaactacct agatctatca cttctgtctc       3480
acgaagagga ggaggaggag accatgcttt tccgcagcac tataaaatac attttcggtt       3540
atatataagt tgctgaccga cgtcggtgtc gtttccctcg aaatctgcat tttctaaatt       3600
ttccatggcc aactaggagg ctgggatttc atcaaagcac gggaaaggtt tttgtcaact       3660
atatcctgtt attagtatat ccgtaagagt tagggttagt gaggccacga tgtttctggg       3720
gtcaagttac aaacaaagtt acgaacccgc agg                                    3753
```

<210> SEQ ID NO 2
<211> LENGTH: 1761
<212> TYPE: DNA
<213> ORGANISM: Penicillium sp. CBS 109899
<220> FEATURE:
<221> NAME/KEY: CDS
<222> LOCATION: (89)..(1711)

<400> SEQUENCE: 2

```
accggacttt caaggtttca tttaacattc attgtccttt ggttcatatt ctatacagaa        60
```

```
gaatcagaac tgtatttcga ttaccacg atg ctc aag cta tat gta gct gcc              112
                                Met Leu Lys Leu Tyr Val Ala Ala
                                 1               5 tgt ctg gtg gtg gcc ggt gtt tct atc ccg aca gac cct acc gta acc             160
Cys Leu Val Val Ala Gly Val Ser Ile Pro Thr Asp Pro Thr Val Thr
     10              15              20 caa gtc ccg gat tac ttc caa acg agc tat ggg cca tat gca ggt gct             208
Gln Val Pro Asp Tyr Phe Gln Thr Ser Tyr Gly Pro Tyr Ala Gly Ala
 25              30              35              40 acc aaa gcc gga ggc gct ccg ttc ctt gcg caa acc aat ccg atc tat             256
Thr Lys Ala Gly Gly Ala Pro Phe Leu Ala Gln Thr Asn Pro Ile Tyr
                 45              50              55 tcc cag ccg acc tac gtc gca aac acg cca ttg gtg aca act ctt ccc             304
Ser Gln Pro Thr Tyr Val Ala Asn Thr Pro Leu Val Thr Thr Leu Pro
             60              65              70 ata tct ggt gaa ccc cat gac gga aac ata ttc ggc tgg atg ggg act             352
Ile Ser Gly Glu Pro His Asp Gly Asn Ile Phe Gly Trp Met Gly Thr
         75              80              85 ttg agt cct tac caa ccc agc cct gat gga ttt ggc gtg gat gaa tat             400
Leu Ser Pro Tyr Gln Pro Ser Pro Asp Gly Phe Gly Val Asp Glu Tyr
         90              95             100 cct ctc cct ccc ggt gca aac att acg caa atc cat atg gtg cat cgc             448
Pro Leu Pro Pro Gly Ala Asn Ile Thr Gln Ile His Met Val His Arg
105             110             115             120 cat ggc tcg cgc tat ccg acg tca aat tcc gca atc agc gat tgg gct             496
His Gly Ser Arg Tyr Pro Thr Ser Asn Ser Ala Ile Ser Asp Trp Ala
                125             130             135 aag aaa ata atg cag tat cga tcc aac ggc aca gtg ttc tca ggc gaa             544
Lys Lys Ile Met Gln Tyr Arg Ser Asn Gly Thr Val Phe Ser Gly Glu
            140             145             150 ctt gag ttt ctg aac gct tgg aac tat cag ctc gga cag gca gag cta             592
Leu Glu Phe Leu Asn Ala Trp Asn Tyr Gln Leu Gly Gln Ala Glu Leu
            155             160             165 aca gca cga ggt cgg caa gag tta ttc gac agc ggg att cta cat tgg             640
Thr Ala Arg Gly Arg Gln Glu Leu Phe Asp Ser Gly Ile Leu His Trp
170             175             180 ttc aat tat gga aag ctc tac gat cct gca tca aaa atc ata gct cgc             688
Phe Asn Tyr Gly Lys Leu Tyr Asp Pro Ala Ser Lys Ile Ile Ala Arg
185             190             195             200 aca aca acg atg gtg agg atg ttg caa tca gcg gag aac ttc ctc aat             736
Thr Thr Thr Met Val Arg Met Leu Gln Ser Ala Glu Asn Phe Leu Asn
                205             210             215 gga ttt ttt ggt cca aac tgg act aat aat gcg acg ctt gaa gtc att             784
Gly Phe Phe Gly Pro Asn Trp Thr Asn Asn Ala Thr Leu Glu Val Ile
            220             225             230 att gaa agt acc ggg ttc aac aac tcc ctc gca ggg aat gat atg tgt             832
Ile Glu Ser Thr Gly Phe Asn Asn Ser Leu Ala Gly Asn Asp Met Cys
            235             240             245 cgc aat gca aaa aat aca tcg ggg ggc gac gca gta aat gaa tgg acc             880
Arg Asn Ala Lys Asn Thr Ser Gly Gly Asp Ala Val Asn Glu Trp Thr
250             255             260 gcg cta tac ttg cag aaa gcg aca aat cgc ttc aga agt gaa ata tct             928
Ala Leu Tyr Leu Gln Lys Ala Thr Asn Arg Phe Arg Ser Glu Ile Ser
265             270             275             280 gga agt ctg aac tgg act gtt gac gac acg tac aat gca cag tcg atg             976
Gly Ser Leu Asn Trp Thr Val Asp Asp Thr Tyr Asn Ala Gln Ser Met
                285             290             295 tgc cca tac gag act gtt gca ctt ggt tat agt ccg ttt tgt aca ttg            1024
Cys Pro Tyr Glu Thr Val Ala Leu Gly Tyr Ser Pro Phe Cys Thr Leu
            300             305             310
```

```
ttt tct tgg gag gaa tgg caa ggg ttc cag tat gtt aac gac ttg aac    1072
Phe Ser Trp Glu Glu Trp Gln Gly Phe Gln Tyr Val Asn Asp Leu Asn
        315                 320                 325 ctc tat ggg aac tat ggc atg ggt tct cca gtt ggc cgc gcc att gga    1120
Leu Tyr Gly Asn Tyr Gly Met Gly Ser Pro Val Gly Arg Ala Ile Gly
    330                 335                 340 ctt gga ttt gtc gaa gaa ttg att gca cgg ctg cag ggg caa atc cca    1168
Leu Gly Phe Val Glu Glu Leu Ile Ala Arg Leu Gln Gly Gln Ile Pro
345                 350                 355                 360 aac ccc cct gaa gac tca att ggg ttc aat caa tcg cta gat gat agt    1216
Asn Pro Pro Glu Asp Ser Ile Gly Phe Asn Gln Ser Leu Asp Asp Ser
                365                 370                 375 gcc gcg act ttc cct ctc aac caa aca atc tac ttc gac ttt agc cac    1264
Ala Ala Thr Phe Pro Leu Asn Gln Thr Ile Tyr Phe Asp Phe Ser His
            380                 385                 390 gac aac gag atg ttc tcg atg ttg act gcc ctg ggc ttg aca cag ttt    1312
Asp Asn Glu Met Phe Ser Met Leu Thr Ala Leu Gly Leu Thr Gln Phe
        395                 400                 405 ggg gac tac ctc tct ccc acg aag ccc tct gcg gat cgt tcg ttg att    1360
Gly Asp Tyr Leu Ser Pro Thr Lys Pro Ser Ala Asp Arg Ser Leu Ile
    410                 415                 420 gga agc cat atc gtc ccg ttc tcg gct acc ttt gta ttt gag atc atc    1408
Gly Ser His Ile Val Pro Phe Ser Ala Thr Phe Val Phe Glu Ile Ile
425                 430                 435                 440 aaa gca cct ggt ctt gta cga gag aat cga tca aag tat tgc ggt gaa    1456
Lys Ala Pro Gly Leu Val Arg Glu Asn Arg Ser Lys Tyr Cys Gly Glu
                445                 450                 455 agt gtg tat gaa aat acg agc gaa gaa aca acc tac ata cat ctc gtc    1504
Ser Val Tyr Glu Asn Thr Ser Glu Glu Thr Thr Tyr Ile His Leu Val
            460                 465                 470 att aac cag agg act gtt cct ctt ggt caa agc att tca gca tgc ggg    1552
Ile Asn Gln Arg Thr Val Pro Leu Gly Gln Ser Ile Ser Ala Cys Gly
        475                 480                 485 caa cga gat gat ggt tgg tgt gaa att tcc gcc ttc att cag gcg cag    1600
Gln Arg Asp Asp Gly Trp Cys Glu Ile Ser Ala Phe Ile Gln Ala Gln
    490                 495                 500 aaa gaa aac atc gtg aag gca aat tac gag gaa agc tgt ttc gga aat    1648
Lys Glu Asn Ile Val Lys Ala Asn Tyr Glu Glu Ser Cys Phe Gly Asn
505                 510                 515                 520 tgg agc atc ccg gcg tac ggc gag atc agg gat ggc gct att ccg aag    1696
Trp Ser Ile Pro Ala Tyr Gly Glu Ile Arg Asp Gly Ala Ile Pro Lys
                525                 530                 535 aat gct acg tcc taa ctgctatatt agacgccctc gaaagtttag attggagata    1751
Asn Ala Thr Ser
            540 ctcggacaaa                                                         1761

<210> SEQ ID NO 3
<211> LENGTH: 540
<212> TYPE: PRT
<213> ORGANISM: Penicillium sp. CBS 109899

<400> SEQUENCE: 3

Met Leu Lys Leu Tyr Val Ala Ala Cys Leu Val Val Ala Gly Val Ser
1               5                   10                  15

Ile Pro Thr Asp Pro Thr Val Thr Gln Val Pro Asp Tyr Phe Gln Thr
            20                  25                  30

Ser Tyr Gly Pro Tyr Ala Gly Ala Thr Lys Ala Gly Gly Ala Pro Phe
        35                  40                  45
```

-continued

```
Leu Ala Gln Thr Asn Pro Ile Tyr Ser Gln Pro Thr Tyr Val Ala Asn
 50                  55                  60

Thr Pro Leu Val Thr Thr Leu Pro Ile Ser Gly Glu Pro His Asp Gly
 65                  70                  75                  80

Asn Ile Phe Gly Trp Met Gly Thr Leu Ser Pro Tyr Gln Pro Ser Pro
                 85                  90                  95

Asp Gly Phe Gly Val Asp Glu Tyr Pro Leu Pro Pro Gly Ala Asn Ile
                100                 105                 110

Thr Gln Ile His Met Val His Arg His Gly Ser Arg Tyr Pro Thr Ser
                115                 120                 125

Asn Ser Ala Ile Ser Asp Trp Ala Lys Lys Ile Met Gln Tyr Arg Ser
130                 135                 140

Asn Gly Thr Val Phe Ser Gly Glu Leu Glu Phe Leu Asn Ala Trp Asn
145                 150                 155                 160

Tyr Gln Leu Gly Gln Ala Glu Leu Thr Ala Arg Gly Arg Gln Glu Leu
                165                 170                 175

Phe Asp Ser Gly Ile Leu His Trp Phe Asn Tyr Gly Lys Leu Tyr Asp
                180                 185                 190

Pro Ala Ser Lys Ile Ile Ala Arg Thr Thr Met Val Arg Met Leu
                195                 200                 205

Gln Ser Ala Glu Asn Phe Leu Asn Gly Phe Phe Gly Pro Asn Trp Thr
210                 215                 220

Asn Asn Ala Thr Leu Glu Val Ile Ile Glu Ser Thr Gly Phe Asn Asn
225                 230                 235                 240

Ser Leu Ala Gly Asn Asp Met Cys Arg Asn Ala Lys Asn Thr Ser Gly
                245                 250                 255

Gly Asp Ala Val Asn Glu Trp Thr Ala Leu Tyr Leu Gln Lys Ala Thr
                260                 265                 270

Asn Arg Phe Arg Ser Glu Ile Ser Gly Ser Leu Asn Trp Thr Val Asp
                275                 280                 285

Asp Thr Tyr Asn Ala Gln Ser Met Cys Pro Tyr Glu Thr Val Ala Leu
                290                 295                 300

Gly Tyr Ser Pro Phe Cys Thr Leu Phe Ser Trp Glu Glu Trp Gln Gly
305                 310                 315                 320

Phe Gln Tyr Val Asn Asp Leu Asn Leu Tyr Gly Asn Tyr Gly Met Gly
                325                 330                 335

Ser Pro Val Gly Arg Ala Ile Gly Leu Gly Phe Val Glu Glu Leu Ile
                340                 345                 350

Ala Arg Leu Gln Gly Gln Ile Pro Asn Pro Pro Glu Asp Ser Ile Gly
                355                 360                 365

Phe Asn Gln Ser Leu Asp Asp Ser Ala Ala Thr Phe Pro Leu Asn Gln
                370                 375                 380

Thr Ile Tyr Phe Asp Phe Ser His Asp Asn Glu Met Phe Ser Met Leu
385                 390                 395                 400

Thr Ala Leu Gly Leu Thr Gln Phe Gly Asp Tyr Leu Ser Pro Thr Lys
                405                 410                 415

Pro Ser Ala Asp Arg Ser Leu Ile Gly Ser His Ile Val Pro Phe Ser
                420                 425                 430

Ala Thr Phe Val Phe Glu Ile Ile Lys Ala Pro Gly Leu Val Arg Glu
                435                 440                 445

Asn Arg Ser Lys Tyr Cys Gly Glu Ser Val Tyr Glu Asn Thr Ser Glu
450                 455                 460
```

```
Glu Thr Thr Tyr Ile His Leu Val Ile Asn Gln Arg Thr Val Pro Leu
465                 470                 475                 480

Gly Gln Ser Ile Ser Ala Cys Gly Gln Arg Asp Asp Gly Trp Cys Glu
                485                 490                 495

Ile Ser Ala Phe Ile Gln Ala Gln Lys Glu Asn Ile Val Lys Ala Asn
            500                 505                 510

Tyr Glu Glu Ser Cys Phe Gly Asn Trp Ser Ile Pro Ala Tyr Gly Glu
        515                 520                 525

Ile Arg Asp Gly Ala Ile Pro Lys Asn Ala Thr Ser
    530                 535                 540

<210> SEQ ID NO 4
<211> LENGTH: 2757
<212> TYPE: DNA
<213> ORGANISM: Penicillium funiculosum

<400> SEQUENCE: 4
tgtattgttg tttgtcgaag tcgatttccc agttgttacg attctagcaa gaagattaat      60
acatgcagtt ctcaaacaaa gctcaaggga catgcttact ccatggcgaa caagatagat     120
ggtgtctaga ggcatcgcat cgaaaggccg tcttggctgt attgatagat ttgattgaac     180
agttgtaagt tctcaatttt tctagccttt atacttctaa aggcaaactc tccatcaaaa     240 gtttgcttc gatacctaca cctggaatcc actttccgat agactgcaat gcccactatg      300
accagtgccc acttgcagtc gccaagtttc atttaacttc ctgagacctt ttttggataa     360
acctaaagca aagcgagccg acataattgc ctcatctgat aaagaatgaa atcaagttta     420
gccaacagcg gataaagcaa tatcgcgcct tggttcttaa taggcgttca gtacctgaca     480
atgcagcttc ttggaccagt tattatcggc aaatgtaaat gcttaggata ggcccaacga     540
actcactaat gaggtcccaa atcggaagtc tccagctacc ccagattgtc aaaagccggg     600
gtaggaatat ggcgctcgct atgttgtcta ttcgggcaga aagtcgtgtg acagagagag     660
ttataaataa ccttggaaag cttcgtaatg acactttgt accggacttc caagattctg      720
ttaacattca ttgttcttct gttcatttga ttttatacaa aagaatcaac agtgtattct     780
cattagcatg atgctcaagc tatgtgtagc tgcctgtttg gtggtggccg gtgtttctat     840
cccgacagac cctacagtaa ctcaagtccc ggattacttc caaacaagct atgggccata     900
tgcaggtatg gtaatacgtg taacttgtca agagtcccca gggctcacag gctataggtg     960
ctactaaagc cggagacgct ccgttccttg cgcaaaccaa cccagtctat tcccagccga    1020
cctatgtcgc aaacacgcca ttggtgacta ctcttcccat atctggtgaa ccccatgacg    1080
ggaacatatt cggctggatg gggactttga ggtatgtatt ctcttgcgct gaagtgccgt    1140
tactacggat ggaactaatt tgatacaaaa cagtccttac cagcccagcc tgatggatt     1200 tggcgtggat gaatatcctc tccctcccgg tgcaaacatt acgcaaatcc atatggtgca    1260
tcgccatggc tcgcgctatc cgacagcaaa ctccgccatt agcagttggg caaagaagat    1320
aatgcagtat cgatccaacg gcaccgtgtt tcaggcgaa cttgattttc tgaacacttg      1380
gaactaccag cttggacagg cagagctaac agcacgaggt cggcaagagt tattcgatag    1440
cggtgttctg cattggttca attatggaaa gctctacgat tctgcgtcga aaatcattgc    1500
tcgtacgaca acgatggtgc ggatgttgca atcggctgag aacttcctca cgggtttttt   1560
tggtccaaac tggaacaata atgcgacact tgaagttatt attgaaagta ccgggttcaa   1620
caactccctc gcagggaatg atatgtgtcc caatgcaaaa aatacatcag gaggcgatgc   1680
```

```
agtagatgaa tggacctcgc tatacttgca gaaagcgaca aatcgcttta gaagtgaaat    1740
atcaggaagc ctgaactgga ctgttgacga cacctacaat gcacaatcta tgtgcccata    1800
tgagacggtt gcccttggtt atagcccgtt ttgcacattg ttttcttggg aggaatggca    1860
agggttccag tatgttaacg atttgaacct ctatgggaat tatggcatgg gatccccagt    1920
aggccgcgcc attgggcttg gattcgtcga agaattaatt gcaaggttgc aaggacaatt    1980
tccaacaccc cctgaagact caattgtttt caatcaatcg ctagatcaga gtgcggcaac    2040
cttccctctc aaccaaacta tctacttcga tttcagccac gacaacgaga tgttctccat    2100
gttaactgcc ctgggcttaa cacaatttgg ggactacctc tctcccacaa agccctctgc    2160
cgatcgttcg ttgattggaa gccatatcgt cccgttctcg gctacctttg tgtttgagat    2220
catcaaagca cctggtcctg tacgagagga tcgatcaaag tattgcggtg aaagtgtgta    2280
tgaaaacact agcgaggaga caacctacat acatctcgtc attaaccaga ggactgttcc    2340
tcttggtcaa agcatttcag catgcggaca acgagatgat ggttggtgtg agatttccgc    2400
cttcattcag gcgcagaaag acaacattga aaggcaaat tacgagcaaa gctgctttgg    2460
aaattggagt atcccggcgt acggccagat tagagatggc gctattccga agaatgccac    2520
ttcctaactg ctatattaga tgcccccgaa agtttagaca ggagatagta ctcgtcagga    2580
ggcccatatc tcagccagcc acagcactgc ggagcgatga agggttgaat atagcacacc    2640
gcggggtgct tgatcccaag tttgggaagc cggatttaga tattttaatt ctctgttagg    2700
tatatttatg ctacgtagct gattttttgtc caatcgacca atttcatctc cgatatc      2757
```

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide PN3

<400> SEQUENCE: 5

```
ccgttggtaa ccagcggagg gatc                                             24
```

<210> SEQ ID NO 6
<211> LENGTH: 24
<212> TYPE: DNA
<213> ORGANISM: Artificial Sequence
<220> FEATURE:
<223> OTHER INFORMATION: Oligonucleotide PN4

<400> SEQUENCE: 6

```
ccttggtccg tgtttcaaga cggg                                             24
```

<210> SEQ ID NO 7
<211> LENGTH: 1175
<212> TYPE: DNA
<213> ORGANISM: Penicillium sp. CBS 109899

<400> SEQUENCE: 7

```
ccgttggtaa ccagcggagg gatcattacc gagtgcgggc cctcgcggcc caacctccca     60
cccttgtctc tatacacctg ttgctttggc gggcccaccg gggccacctg gtcgccgggg    120
gacgcacgtc cccgggcccg cgcccgccga agcgcgctgt gaaccctgat gaagatgggc    180
tgtctgagta ctatgaaaat tgtcaaaact ttcaacaatg gatctcttgg ttccggcatc    240
gatgaagaac gcagcgaaat gcgataagta atgtgaattg cagaattccg tgaatcatcg    300
aatctttgaa cgcacattgc gcccccctggc attccggggg gcatgcctgt ccgagcgtca    360
```

-continued

```
tttctgccct caagcacggc tggtgtgttg ggtgtggtcc ccccggggac ctgcccgaaa      420
ggcagcggcg acgtccgtct ggtcctcgag cgtatggggc tctgtcactc gctcgggaag      480
gacctgcggg ggttggtcac caccacattt taccacggtt gacctcggat caggtaggag      540
ttacccgctg aacttaagca tatcaataag cggaggaaaa gaaaccaacc gggattgcct      600
cagtaacggc gagtgaagcg gcaagagctc aaatttgaaa tctggcccct ttggggtccg      660
agttgtaatt tgcagaggat gcttcgggtg cggtccccgt ctaagtgccc tggaacgggc      720
cgtcatagag ggtgagaatc ccgtctggga tgggcggccg cgcccgtgtg aagctccttc      780
gacgagtcga gttgtttggg aatgcagctc taagcgggtg gtaaatttca tctaaagcta      840
aatactggcc ggagaccgat agcgcacaag tagagtgatc gaaagatgaa agcactttg       900 aaaagagagt taaacagcac gtgaaattgt tgaaagggaa gcgttgtcca ccagactcgc      960 ccggggggt tcagccggca cgtgtgccgg tgtactcctc tccgggcggg ccagcatcgg      1020
tttgggcggc tggtgaaagg ccccgggaat gtaacaccct tcggggtgcc ttatagcccg     1080
gggtgccata cagccagcct ggaccgaggc ccgcgcttcg gcgaggatgc tggcgtaatg     1140
gtggtcaacg gcccgtcttg aaacacggac caagg                                1175
```

<210> SEQ ID NO 8
<211> LENGTH: 11
<212> TYPE: PRT
<213> ORGANISM: Penicillium sp. CBS 109899
<220> FEATURE:
<221> NAME/KEY: MISC_FEATURE
<222> LOCATION: (9)..(9)
<223> OTHER INFORMATION: Xaa = Gln or Val

<400> SEQUENCE: 8

```
Ile Pro Thr Asp Pro Gln Val Pro Xaa Tyr Phe
1               5                   10
```

<210> SEQ ID NO 9
<211> LENGTH: 17
<212> TYPE: PRT
<213> ORGANISM: Penicillium sp. CBS 109899

<400> SEQUENCE: 9

```
Thr Ser Gly Gly Asp Ala Val Asn Glu Trp Thr Ala Leu Tyr Leu Gln
1               5                   10                  15

Lys
```

<210> SEQ ID NO 10
<211> LENGTH: 20
<212> TYPE: PRT
<213> ORGANISM: Penicillium sp. CBS 109899
<220> FEATURE:
<221> NAME/KEY: MISC_FEATURE
<222> LOCATION: (10)..(10)
<223> OTHER INFORMATION: Xaa = any amino acid
<220> FEATURE:
<221> NAME/KEY: MISC_FEATURE
<222> LOCATION: (15)..(15)
<223> OTHER INFORMATION: Xaa = any amino acid
<220> FEATURE:
<221> NAME/KEY: MISC_FEATURE
<222> LOCATION: (18)..(18)
<223> OTHER INFORMATION: Xaa = any amino acid

<400> SEQUENCE: 10

```
Ala Gly Gly Ala Pro Phe Leu Ala Gln Xaa Asn Pro Ile Tyr Xaa Gln
1               5                   10                  15
```

Pro Xaa Tyr Val
        20

<210> SEQ ID NO 11
<211> LENGTH: 7
<212> TYPE: PRT
<213> ORGANISM: Penicillium sp. CBS 109899

<400> SEQUENCE: 11

Leu Tyr Asp Pro Ala Ser Lys
1               5

<210> SEQ ID NO 12
<211> LENGTH: 6
<212> TYPE: PRT
<213> ORGANISM: Penicillium sp. CBS 109899

<400> SEQUENCE: 12

Ala Pro Gly Leu Val Arg
1               5

<210> SEQ ID NO 13
<211> LENGTH: 17
<212> TYPE: DNA
<213> ORGANISM: Artificial Sequence
<220> FEATURE:
<223> OTHER INFORMATION: Oligonucleotide OT ACS 17 P4.4
<220> FEATURE:
<221> NAME/KEY: misc_feature
<222> LOCATION: (3)..(3)
<223> OTHER INFORMATION: n = a or g or c or t
<220> FEATURE:
<221> NAME/KEY: misc_feature
<222> LOCATION: (6)..(6)
<223> OTHER INFORMATION: y = t or c
<220> FEATURE:
<221> NAME/KEY: misc_feature
<222> LOCATION: (9)..(9)
<223> OTHER INFORMATION: n = a or g or c or t
<220> FEATURE:
<221> NAME/KEY: misc_feature
<222> LOCATION: (12)..(12)
<223> OTHER INFORMATION: r = g or a

<400> SEQUENCE: 13
acngayccnc argtccc                                                    17

<210> SEQ ID NO 14
<211> LENGTH: 17
<212> TYPE: DNA
<213> ORGANISM: Artificial Sequence
<220> FEATURE:
<223> OTHER INFORMATION: Oligonucleotide OT ACS 25 P6.1
<220> FEATURE:
<221> NAME/KEY: misc_feature
<222> LOCATION: (3)..(3)
<223> OTHER INFORMATION: n = a or g or c or t
<220> FEATURE:
<221> NAME/KEY: misc_feature
<222> LOCATION: (9)..(9)
<223> OTHER INFORMATION: y = t or c
<220> FEATURE:
<221> NAME/KEY: misc_feature
<222> LOCATION: (12)..(12)
<223> OTHER INFORMATION: r = g or a
<220> FEATURE:
<221> NAME/KEY: misc_feature
<222> LOCATION: (15)..(15)
<223> OTHER INFORMATION: n = a or g or c or t

```
<400> SEQUENCE: 14
gcngtccayt crttnac                                                   17

<210> SEQ ID NO 15
<211> LENGTH: 846
<212> TYPE: DNA
<213> ORGANISM: Penicillium sp. CBS 109899

<400> SEQUENCE: 15
acagatcccc aggtcccgga ttacttccaa acgagctatg ggccatatgc aggtatggaa    60
atatgcgtac cctgacaaag gctattaggg ctcaacaggc tacaggtgct accaaagccg   120
gaggcgctcc gttccttgcg caaaccaatc cgatctattc ccagccgacc tacgtcgcaa   180
acacgccatt ggtgacaact cttcccatat ctggtgaacc ccatgacgga aacatattcg   240
gctggatggg gactttgagg tatgtattat ctttcgctga agtaccgtta gtacggatga   300
aactgatctt agacaaaaca gtccttacca acccagccct gatggatttg cgtggatga    360 atatcctctc cctcccggtg caaacattac gcaaatccat atggtgcatc gccatggctc   420
gcgctatccg acgtcaaatt ccgcaatcag cgattgggca agaaaataa tgcagtatcg    480 atccaacggc acagtgttct caggcgaact tgagtttctg aacgcttgga actatcagct   540
cggacaggca gagctaacag cacgaggtcg gcaagagtta ttcgacagcg ggattctaca   600
ttggttcaat tatggaaagc tctacgatcc tgcatcaaaa atcatagctc gcacaacaac   660
gatggtgagg atgttgcaat cagcggagaa cttcctcaat ggatttttg gtccaaactg    720 gactaataat gcgacgcttg aagtcattat tgaaagtacc gggtttaaca actccctcgc   780
agggaatgat aagtgtcgca atgcaaaaaa tacatcgggg ggcgacgcag taaatgaatg   840
gaccgc                                                             846

<210> SEQ ID NO 16
<211> LENGTH: 27
<212> TYPE: DNA
<213> ORGANISM: Artificial Sequence
<220> FEATURE:
<223> OTHER INFORMATION: Oligonucleotide OT ACS 32 P5

<400> SEQUENCE: 16
ccatcagggc tgggttggta aggactg                                        27

<210> SEQ ID NO 17
<211> LENGTH: 28
<212> TYPE: DNA
<213> ORGANISM: Artificial Sequence
<220> FEATURE:
<223> OTHER INFORMATION: Oligonucleotide OT ACS 32 P3

<400> SEQUENCE: 17
ctggactatt aatgcgacgc ttgaggtc                                       28

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide OT ACS 38 P1

<400> SEQUENCE: 18
ggctttgctg gtgcggggtc agtc                                           24
```

-continued

<210> SEQ ID NO 19
<211> LENGTH: 33
<212> TYPE: DNA
<213> ORGANISM: Artificial Sequence
<220> FEATURE:
<223> OTHER INFORMATION: Oligonucleotide OT ACS 38 P2

<400> SEQUENCE: 19
cctgcgggtt cgtaactttg tttgtaactt gac                                    33

<210> SEQ ID NO 20
<211> LENGTH: 23
<212> TYPE: DNA
<213> ORGANISM: Artificial Sequence
<220> FEATURE:
<223> OTHER INFORMATION: Oligonucleotide OT ACS 37 P1

<400> SEQUENCE: 20
ggcgctccgt tccttgcgca aac                                               23

<210> SEQ ID NO 21
<211> LENGTH: 23
<212> TYPE: DNA
<213> ORGANISM: Artificial Sequence
<220> FEATURE:
<223> OTHER INFORMATION: Oligonucleotide OT ACS 37 P3

<400> SEQUENCE: 21
gtaggtcggc tgggaataga tcg                                               23

<210> SEQ ID NO 22
<211> LENGTH: 34
<212> TYPE: DNA
<213> ORGANISM: Artificial Sequence
<220> FEATURE:
<223> OTHER INFORMATION: Oligonucleotide phyGoamp4

<400> SEQUENCE: 22
tagatatcac gatgctcaag ctatatgtag ctgc                                   34

<210> SEQ ID NO 23
<211> LENGTH: 34
<212> TYPE: DNA
<213> ORGANISM: Artificial Sequence
<220> FEATURE:
<223> OTHER INFORMATION: Oligonucleotide phyGoamp5

<400> SEQUENCE: 23
atactagttt aggacgtagc attcttcgga atag                                   34

<210> SEQ ID NO 24
<211> LENGTH: 7
<212> TYPE: PRT
<213> ORGANISM: Artificial Sequence
<220> FEATURE:
<223> OTHER INFORMATION: Specific Sites for Binding in SEQ ID NO: 3
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Xaa = any amino acid

```
-continued

<400> SEQUENCE: 24

Arg His Gly Xaa Arg Xaa Pro
1               5
```